United States Patent
Ogle

(10) Patent No.: US 11,229,445 B2
(45) Date of Patent: Jan. 25, 2022

(54) HYDRAULIC DISPLACEMENT AND REMOVAL OF THROMBUS CLOTS, AND CATHETERS FOR PERFORMING HYDRAULIC DISPLACEMENT

(71) Applicant: MIVI Neuroscience, Inc., Eden Prairie, MN (US)

(72) Inventor: Matthew F. Ogle, Edina, MN (US)

(73) Assignee: MIVI Neuroscience, Inc., Eden Prairie, MN (US)

(*) Notice: Subject to any disclaimer, the term of this patent is extended or adjusted under 35 U.S.C. 154(b) by 428 days.

(21) Appl. No.: 15/725,970

(22) Filed: Oct. 5, 2017

(65) Prior Publication Data
US 2018/0098778 A1   Apr. 12, 2018

Related U.S. Application Data

(60) Provisional application No. 62/404,918, filed on Oct. 6, 2016.

(51) Int. Cl.
*A61B 17/22* (2006.01)
*A61M 25/00* (2006.01)
(Continued)

(52) U.S. Cl.
CPC .... *A61B 17/22* (2013.01); *A61B 2017/22038* (2013.01); *A61B 2017/22062* (2013.01);
(Continued)

(58) Field of Classification Search
CPC .......... A61B 17/22; A61B 2017/22001; A61B 2017/22002; A61B 2017/22038;
(Continued)

(56) References Cited

U.S. PATENT DOCUMENTS

| 2,730,101 A | 1/1956 | Hoffman |
| 3,949,757 A | 4/1976 | Sabel |

(Continued)

FOREIGN PATENT DOCUMENTS

| EP | 0117940 A2 | 9/1984 |
| EP | 1226795 A2 | 7/2002 |

(Continued)

OTHER PUBLICATIONS

Feldman, "Transcatheter Aspiration of a Thrombus in an Aortocoronary Saphenous Vein Graft," American Journal of Cardiology, 60(4)1379-380 (1987).

(Continued)

*Primary Examiner* — Emily L Schmidt
*Assistant Examiner* — Leah J Swanson
(74) *Attorney, Agent, or Firm* — Christensen Fonder Dardi; Andrew H. Auderieth; Peter S. Dardi

(57) ABSTRACT

Clot removal from a patient's vessel, such as an artery, are described using aspiration and hydraulic forces supporting the removal process. Hydraulic forces can be generated by occluding the vessel distal to the clot and delivering liquid between the clot and the occlusive device. The aspiration catheter is positioned proximal to the clot. Catheters designed to facilitate the delivery of hydraulic forces can be based on single lumen designs or dual lumen designs. The catheters may have a fixed internal wire, or in some embodiments the catheters can ride over a wire with a valve/seal positioned to restrict flow into or out from the guide lumen such that the guide lumen can further function for balloon inflation and/or for infusion of liquid.

18 Claims, 15 Drawing Sheets

(51) Int. Cl.
   *A61M 25/01* (2006.01)
   *A61M 25/10* (2013.01)
   *A61F 2/01* (2006.01)

(52) U.S. Cl.
   CPC ........... *A61B 2017/22067* (2013.01); *A61B 2017/22079* (2013.01); *A61B 2017/22082* (2013.01); *A61B 2017/22084* (2013.01); *A61F 2/013* (2013.01); *A61M 25/007* (2013.01); *A61M 25/0021* (2013.01); *A61M 25/0108* (2013.01); *A61M 2025/0031* (2013.01); *A61M 2025/0042* (2013.01); *A61M 2025/1052* (2013.01)

(58) Field of Classification Search
   CPC ........... A61B 2017/22048; A61B 2017/22051; A61B 2017/22062; A61B 2017/22065; A61B 2017/22067; A61B 2017/22079; A61B 2017/22082; A61B 2017/22084; A61B 2017/22047; A61B 2017/22081; A61B 2017/22094; A61M 25/10; A61M 25/104; A61M 25/0021; A61M 25/0023; A61M 25/0026; A61M 25/0028; A61M 25/0029; A61M 25/003; A61M 25/0043; A61M 25/0067; A61M 25/0068; A61M 25/007; A61M 25/0071; A61M 25/0074; A61M 25/0075; A61M 25/0169; A61M 25/0172; A61M 2025/0004; A61M 2025/0031; A61M 2025/0039; A61M 2025/0042; A61M 2025/0079; A61M 2025/0183; A61M 2025/105; A61M 2025/0152
   See application file for complete search history.

(56) References Cited

U.S. PATENT DOCUMENTS

| | | |
|---|---|---|
| 3,996,938 A | 12/1976 | Clark, III |
| 4,020,829 A | 5/1977 | Wilson et al. |
| 4,033,331 A | 7/1977 | Guss et al. |
| 4,174,715 A | 11/1979 | Hasson |
| 4,610,662 A | 9/1986 | Weikl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engleson |
| 4,784,636 A | 11/1988 | Rydell |
| 4,790,812 A | 12/1988 | Hawkins, Jr. et al. |
| 4,794,928 A | 1/1989 | Kletschka |
| 4,795,434 A | 1/1989 | Kujawski |
| 4,799,496 A | 1/1989 | Hargreaves et al. |
| 4,834,709 A | 5/1989 | Banning et al. |
| 4,863,431 A | 9/1989 | Vaillancourt |
| 4,873,978 A | 10/1989 | Ginsburg |
| 4,873,979 A | 10/1989 | Ginsburg |
| 4,883,460 A | 11/1989 | Zanetti |
| 4,887,613 A | 12/1989 | Farr et al. |
| 4,900,303 A | 2/1990 | Lemelson |
| 4,921,484 A | 5/1990 | Hillstead |
| 4,994,067 A | 2/1991 | Summers |
| 4,998,919 A | 3/1991 | Schnepp-Pesch et al. |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Fa |
| 5,102,415 A | 4/1992 | Guenther et al. |
| 5,108,419 A | 4/1992 | Reger et al. |
| 5,152,277 A | 10/1992 | Honda et al. |
| 5,161,534 A | 11/1992 | Berthaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,211,651 A | 5/1993 | Reger et al. |
| 5,219,332 A | 6/1993 | Nelson et al. |
| 5,259,839 A | 11/1993 | Burns |
| 5,308,318 A | 5/1994 | Plassche, Jr. |
| 5,312,338 A | 5/1994 | Nelson et al. |
| 5,325,868 A | 7/1994 | Kimmelstiel |
| 5,352,197 A | 10/1994 | Hammersmark et al. |
| 5,392,778 A | 2/1995 | Horzewski |
| 5,395,383 A | 3/1995 | Adams et al. |
| 5,423,331 A | 6/1995 | Wysham |
| 5,423,745 A | 6/1995 | Todd et al. |
| 5,438,993 A | 8/1995 | Lynch et al. |
| 5,465,716 A | 11/1995 | Avitall |
| 5,485,667 A | 1/1996 | Kleshinski |
| 5,490,859 A | 2/1996 | Mische et al. |
| 5,501,694 A | 3/1996 | Resseman et al. |
| 5,507,732 A | 4/1996 | McClure et al. |
| 5,527,292 A | 6/1996 | Adams et al. |
| 5,533,967 A | 7/1996 | Irman |
| 5,546,958 A | 8/1996 | Thorud et al. |
| 5,549,626 A | 8/1996 | Miller et al. |
| 5,571,122 A | 11/1996 | Kelly et al. |
| 5,578,009 A | 11/1996 | Kraus et al. |
| 5,599,307 A | 2/1997 | Bacher et al. |
| 5,720,764 A | 2/1998 | Naderlinger |
| 5,766,191 A | 6/1998 | Trerotola |
| 5,776,142 A | 7/1998 | Gunderson |
| 5,810,874 A | 9/1998 | Lefebvre |
| 5,814,064 A | 9/1998 | Daniel et al. |
| 5,817,101 A | 10/1998 | Fiedler |
| 5,836,838 A | 11/1998 | Resseman et al. |
| 5,843,002 A | 12/1998 | Pecor et al. |
| 5,843,051 A | 12/1998 | Adams et al. |
| 5,851,189 A | 12/1998 | Forber |
| 5,882,329 A | 3/1999 | Patterson et al. |
| 5,897,567 A | 4/1999 | Resseman et al. |
| 5,899,890 A | 5/1999 | Chiang et al. |
| 5,910,154 A | 6/1999 | Tsguita et al. |
| 5,911,725 A | 6/1999 | Boury |
| 5,911,734 A | 6/1999 | Tsguita et al. |
| 5,928,260 A | 7/1999 | Chin et al. |
| 5,935,139 A | 8/1999 | Bates |
| 5,938,645 A | 8/1999 | Gordon |
| 5,941,869 A | 8/1999 | Patterson et al. |
| 5,972,019 A | 10/1999 | Engleson et al. |
| 5,997,557 A | 12/1999 | Barbut et al. |
| 6,010,522 A | 1/2000 | Barbut et al. |
| 6,015,402 A | 1/2000 | Sahota |
| 6,022,336 A | 2/2000 | Zando-Azizi et al. |
| 6,030,349 A | 2/2000 | Wilson et al. |
| 6,030,369 A | 2/2000 | Engleson et al. |
| 6,066,149 A | 5/2000 | Samson et al. |
| 6,106,530 A | 8/2000 | Harada |
| 6,117,141 A | 9/2000 | Ouchi |
| 6,135,991 A | 10/2000 | Muni et al. |
| 6,142,987 A | 11/2000 | Tsugita |
| 6,146,396 A | 11/2000 | Konya et al. |
| 6,156,005 A | 12/2000 | Theron |
| 6,159,195 A | 12/2000 | Ha et al. |
| 6,168,579 B1 | 1/2001 | Tsugita |
| 6,203,561 B1 | 3/2001 | Ramee et al. |
| 6,206,868 B1 | 3/2001 | Parodi |
| 6,221,049 B1 | 4/2001 | Selmon et al. |
| 6,238,402 B1 | 5/2001 | Sullivan, III et al. |
| 6,238,412 B1 | 5/2001 | Dubrul et al. |
| 6,240,231 B1 | 5/2001 | Ferrera et al. |
| 6,258,115 B1 | 7/2001 | Dubrul |
| 6,270,477 B1 | 8/2001 | Bagaosian et al. |
| 6,277,139 B1 | 8/2001 | Levinson et al. |
| 6,306,124 B1 | 10/2001 | Jones et al. |
| 6,306,163 B1 | 10/2001 | Fitz |
| 6,346,116 B1 | 2/2002 | Brooks et al. |
| 6,361,545 B1 | 3/2002 | Macoviak et al. |
| 6,364,894 B1 | 4/2002 | Healy et al. |
| 6,368,338 B1 | 4/2002 | Konya et al. |
| 6,391,044 B1 | 5/2002 | Yadav et al. |
| 6,432,091 B1 | 8/2002 | Davey |

(56) References Cited

U.S. PATENT DOCUMENTS

| | | |
|---|---|---|
| 6,454,741 B1 | 9/2002 | Muni et al. |
| 6,454,775 B1 | 9/2002 | Demarais et al. |
| 6,485,466 B2 | 11/2002 | Hamilton |
| 6,485,500 B1 | 11/2002 | Kokish et al. |
| 6,485,501 B1 | 11/2002 | Green |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,537,295 B2 | 3/2003 | Petersen |
| 6,540,768 B1 | 4/2003 | Diaz et al. |
| 6,551,302 B1 | 4/2003 | Rosinko et al. |
| 6,558,405 B1 | 5/2003 | McInnes |
| 6,562,020 B1 | 5/2003 | Constanz et al. |
| 6,569,148 B2 | 5/2003 | Bagaosian et al. |
| 6,575,932 B1 | 6/2003 | O'Brien et al. |
| 6,579,484 B1 | 6/2003 | Tiernan et al. |
| 6,589,262 B1 | 7/2003 | Honebrink et al. |
| 6,596,011 B2 | 7/2003 | Johnson et al. |
| 6,610,077 B1 | 8/2003 | Hancock et al. |
| 6,616,681 B2 | 9/2003 | Hanson et al. |
| 6,620,148 B1 | 9/2003 | Tsugita |
| 6,663,613 B1 | 12/2003 | Evans et al. |
| 6,695,865 B2 | 2/2004 | Boyle et al. |
| 6,702,834 B1 | 3/2004 | Boylan et al. |
| 6,736,827 B1 | 5/2004 | McAndrew et al. |
| 6,773,448 B2 | 8/2004 | Kusleika et al. |
| 6,805,684 B2 | 10/2004 | Bonnette et al. |
| 6,805,692 B2 | 10/2004 | Muni et al. |
| 6,824,553 B1 | 11/2004 | Samson et al. |
| 6,866,669 B2 | 3/2005 | Buzzard et al. |
| 6,878,151 B2 | 4/2005 | Garrison et al. |
| 6,879,854 B2 | 4/2005 | Windheuser et al. |
| 6,911,036 B2 | 6/2005 | Douk et al. |
| 6,945,956 B2 | 9/2005 | Waldhauser et al. |
| 6,949,104 B2 | 9/2005 | Griffis et al. |
| 6,951,570 B2 | 10/2005 | Linder et al. |
| 6,958,059 B2 | 10/2005 | Zando-Azizi |
| 6,969,395 B2 | 11/2005 | Eskuri |
| 6,991,642 B2 | 1/2006 | Petersen |
| 7,052,500 B2 | 5/2006 | Bashiri et al. |
| 7,056,328 B2 | 6/2006 | Arnott |
| 7,115,134 B2 | 10/2006 | Chambers |
| 7,115,138 B2 | 10/2006 | Renati et al. |
| 7,166,120 B2 | 1/2007 | Kusleika |
| 7,220,271 B2 | 5/2007 | Clubb et al. |
| 7,229,431 B2 | 6/2007 | Houser et al. |
| 7,229,463 B2 | 6/2007 | Sutton et al. |
| 7,229,464 B2 | 6/2007 | Hanson et al. |
| 7,232,452 B2 | 6/2007 | Adams et al. |
| 7,309,334 B2 | 12/2007 | von Hoffmann |
| 7,329,278 B2 | 2/2008 | Seguin et al. |
| 7,549,974 B2 | 6/2009 | Nayak |
| 7,763,655 B2 | 6/2010 | Itou et al. |
| 7,842,055 B2 | 11/2010 | Pintor et al. |
| 7,879,062 B2 | 2/2011 | Galdonik et al. |
| 7,938,820 B2 | 5/2011 | Webster et al. |
| 8,021,351 B2 | 7/2011 | Boldenow et al. |
| 8,048,032 B2 | 11/2011 | Root et al. |
| 8,092,483 B2 | 1/2012 | Galdonik et al. |
| 8,231,600 B2 | 7/2012 | von Hoffmann |
| 8,308,712 B2 | 11/2012 | Provost et al. |
| 8,419,786 B2 | 4/2013 | Cottone, Jr. et al. |
| 8,764,813 B2 | 7/2014 | Jantzen et al. |
| 8,795,305 B2 | 8/2014 | Martin et al. |
| 8,814,892 B2 | 8/2014 | Galdonik et al. |
| 9,174,025 B2 | 11/2015 | Mallaby |
| 9,561,345 B2 | 2/2017 | Garrison et al. |
| 9,662,129 B2 | 5/2017 | Galdonik et al. |
| 10,213,582 B2 | 2/2019 | Garrison et al. |
| 2001/0044632 A1 | 11/2001 | Daniel et al. |
| 2001/0051811 A1 | 12/2001 | Bonnette et al. |
| 2002/0035347 A1 | 3/2002 | Bagaosian et al. |
| 2002/0055747 A1 | 5/2002 | Cano et al. |
| 2002/0062133 A1 | 5/2002 | Gilson et al. |
| 2002/0095174 A1 | 7/2002 | Tsugita et al. |
| 2002/0111648 A1 | 8/2002 | Kusleika et al. |
| 2002/0133111 A1 | 9/2002 | Shadduck |
| 2002/0143362 A1 | 10/2002 | Mackoviak et al. |
| 2002/0151927 A1 | 10/2002 | Douk et al. |
| 2002/0165574 A1 | 11/2002 | Ressemann et al. |
| 2002/0169472 A1 | 11/2002 | Douk et al. |
| 2002/0183782 A1 | 12/2002 | Tsugita et al. |
| 2003/0023263 A1 | 1/2003 | Krolik et al. |
| 2003/0065353 A1 | 4/2003 | Horzewski et al. |
| 2003/0120208 A1 | 6/2003 | Houser et al. |
| 2003/0135232 A1 | 7/2003 | Douk et al. |
| 2004/0002680 A1 | 1/2004 | Ackerman et al. |
| 2004/0006344 A1 | 1/2004 | Nguyen et al. |
| 2004/0006365 A1 | 1/2004 | Brady et al. |
| 2004/0015151 A1 | 1/2004 | Chambers |
| 2004/0064130 A1 | 4/2004 | Carter |
| 2004/0093044 A1 | 5/2004 | Rychnovsky et al. |
| 2004/0153118 A1 | 8/2004 | Clubb et al. |
| 2004/0220611 A1 | 11/2004 | Ogle |
| 2004/0254602 A1 | 12/2004 | Lehe et al. |
| 2005/0021075 A1 | 1/2005 | Bonnette et al. |
| 2005/0021152 A1 | 1/2005 | Ogle et al. |
| 2005/0059938 A1* | 3/2005 | Malisch ............... A61M 29/00 |
| | | 604/265 |
| 2005/0085847 A1 | 4/2005 | Galdonik et al. |
| 2005/0209631 A1 | 9/2005 | Galdonik et al. |
| 2005/0228479 A1 | 10/2005 | Pavcnik et al. |
| 2005/0277976 A1 | 12/2005 | Galdonik et al. |
| 2006/0030876 A1 | 2/2006 | Peacock, III et al. |
| 2006/0047301 A1 | 3/2006 | Ogle |
| 2006/0129091 A1 | 6/2006 | Bonnette et al. |
| 2006/0200047 A1 | 9/2006 | Galdonik et al. |
| 2006/0200191 A1 | 9/2006 | Zando-Azizi |
| 2007/0060908 A1 | 3/2007 | Webster et al. |
| 2007/0060911 A1 | 3/2007 | Webster et al. |
| 2007/0060944 A1 | 3/2007 | Boldenow et al. |
| 2007/0135733 A1 | 6/2007 | Soukup et al. |
| 2007/0250040 A1 | 10/2007 | Provost et al. |
| 2007/0250096 A1 | 10/2007 | Yamane et al. |
| 2007/0260115 A1 | 11/2007 | Brock et al. |
| 2008/0086110 A1 | 4/2008 | Galdonik et al. |
| 2008/0109088 A1 | 5/2008 | Galdonik et al. |
| 2008/0172066 A9 | 7/2008 | Galdonik et al. |
| 2010/0204672 A1 | 8/2010 | Lockhart et al. |
| 2012/0123466 A1 | 5/2012 | Porter et al. |
| 2012/0253313 A1 | 10/2012 | Galdonik et al. |
| 2013/0245552 A1 | 9/2013 | Ogle et al. |
| 2015/0173782 A1* | 6/2015 | Garrison ............... A61F 2/013 |
| | | 606/127 |
| 2015/0209557 A1 | 7/2015 | Tal et al. |
| 2016/0144157 A1 | 5/2016 | Gulachenski et al. |
| 2016/0199620 A1 | 7/2016 | Pokorney et al. |
| 2017/0056061 A1 | 3/2017 | Ogle et al. |
| 2017/0143938 A1 | 5/2017 | Ogle et al. |

FOREIGN PATENT DOCUMENTS

| | | |
|---|---|---|
| GB | 2020557 A2 | 11/1979 |
| JP | 2014-521462 A | 8/2014 |
| WO | 95-05209 A1 | 2/1995 |
| WO | 98-38930 A1 | 9/1998 |
| WO | 00-16705 A1 | 3/2000 |
| WO | 02-055146 A1 | 7/2002 |
| WO | 02-085092 A2 | 10/2002 |
| WO | 2013-0022796 A2 | 2/2013 |

OTHER PUBLICATIONS

Penumbra, Inc., "Penumbra, Inc. Completes Pivotal Stroke Trial of Intracranial Revascularization" Press Release (2007).

Penumbra, Inc., "The Penumbra Pivotal Stroke Trial: Safety and Effectiveness of a New Generation of Mechanical Devices for Clot Removal in Intracranial Large Vessel Occlusive Disease," Stroke, 40:2761-2768 (2009).

Penumbra, Inc., "The Penumbra System®: Continuous Aspiration Thrombectomy (CAT)," Marketing Brochure © 2010.

(56) References Cited

OTHER PUBLICATIONS

Penumbra, Inc., "5Max™: Direct Aspiration™ Enables Choice," Marketing brochure © 2013.

Reeder et al., "Aspiration Thrombectomy for Removal of Coronary Thrombosis," American Journal of Cardiology, 70:107-110 (Jul. 1, 1992) (Abstract only).

Webb et al., "Retrieval and Analysis of Particulate Debris After Saphenous Vein Graft Intervention," Journal of the American College of Cardiology, 34(2);468-475 (1999).

Yoo et al., "The Penumbra Stroke System: a technical review," Journal of NeuroInterventional Surgery, 4:199-205 (2012).

Abstracts from the 2007 International Stroke Conference, Stroke, 38(2):453-607 (2007).

Search Report from co-pending European Application No. 17859119 dated Apr. 9, 2020.

Search Report from co-pending European Application No. 17859119 dated Mar. 31, 2020.

Office Action from corresponding Japanese Patent Application No. 2019-517974 dated Jun. 22, 2021.

\* cited by examiner

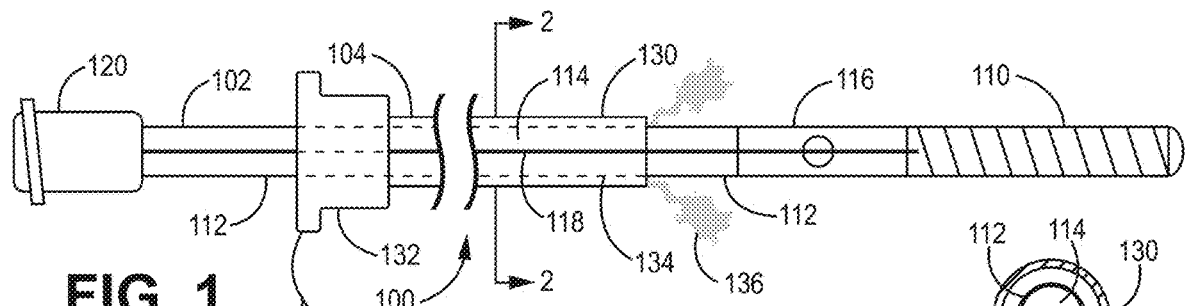
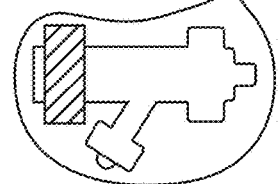
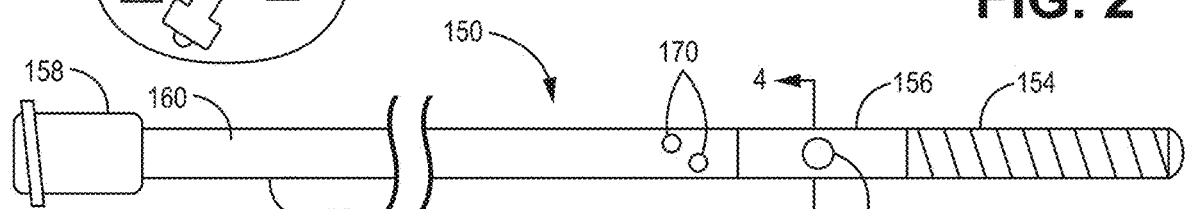
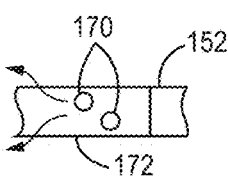
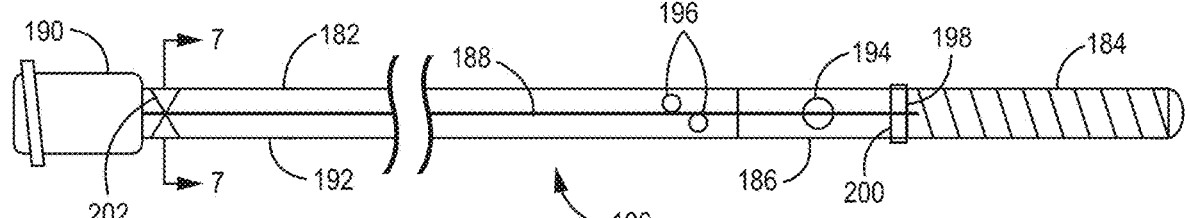
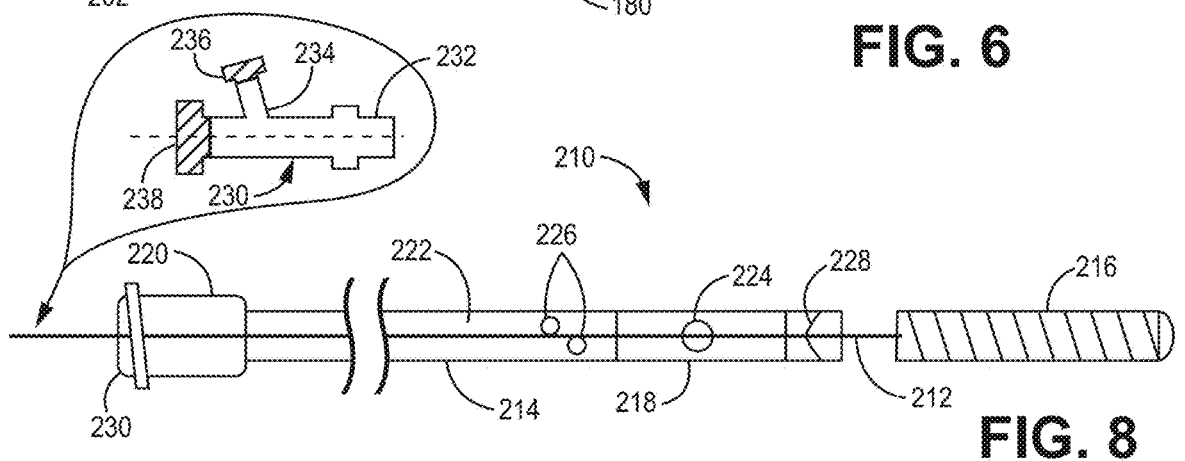

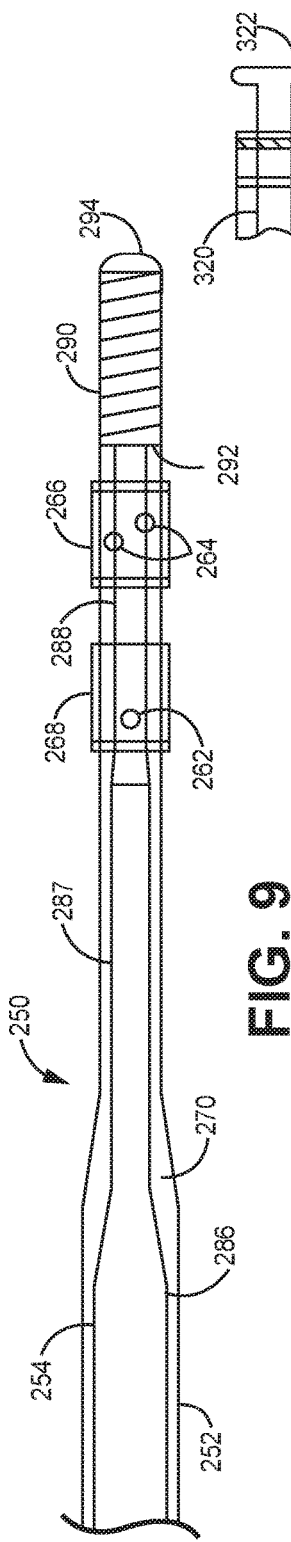
FIG. 9
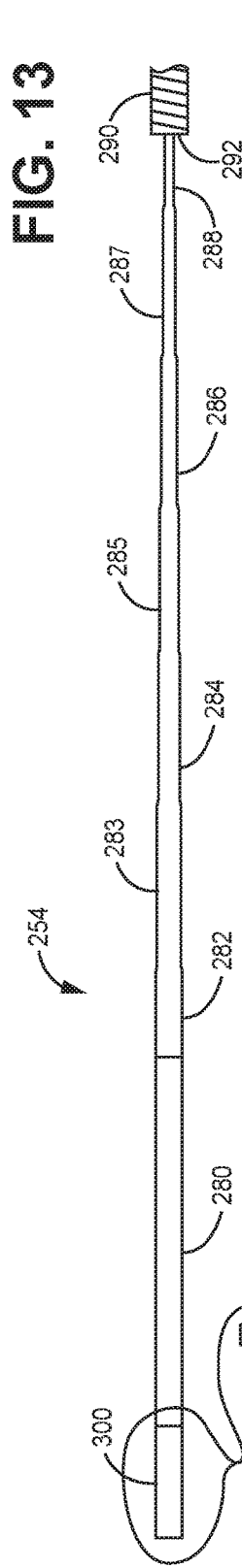
FIG. 10
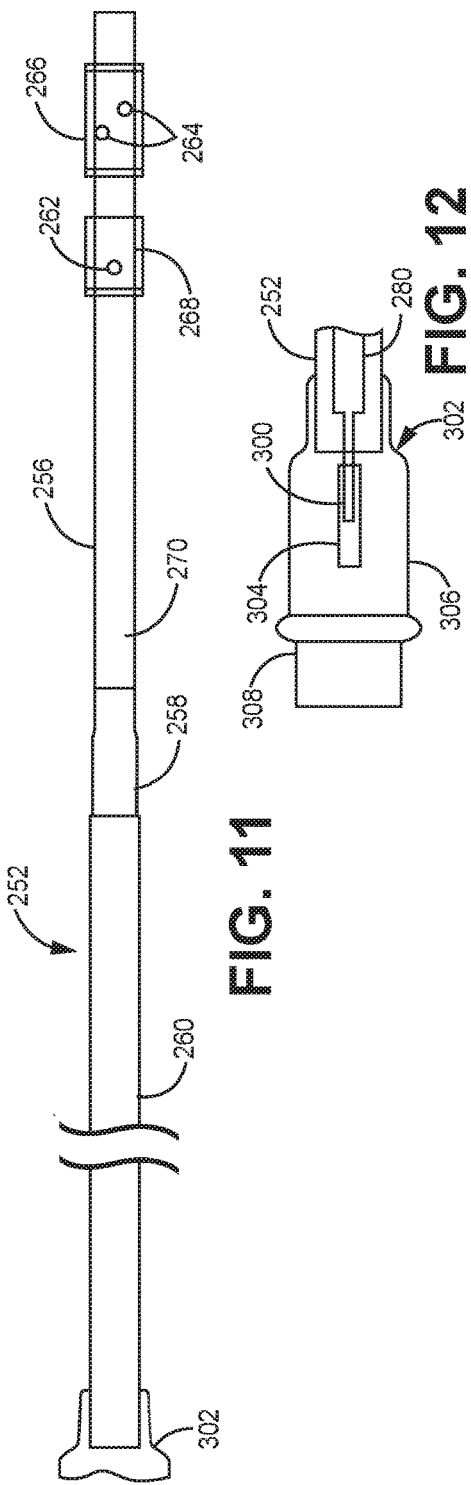
FIG. 11
FIG. 12
FIG. 13

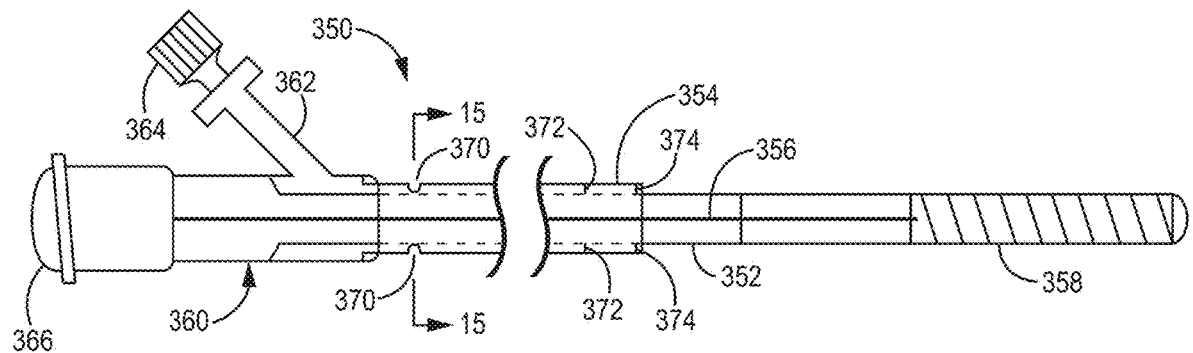
FIG. 14
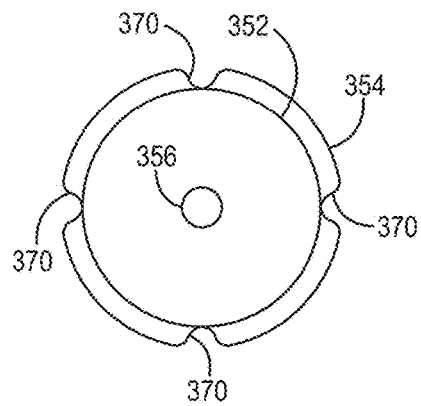
FIG. 15
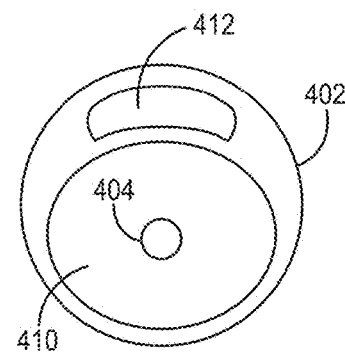
FIG. 17
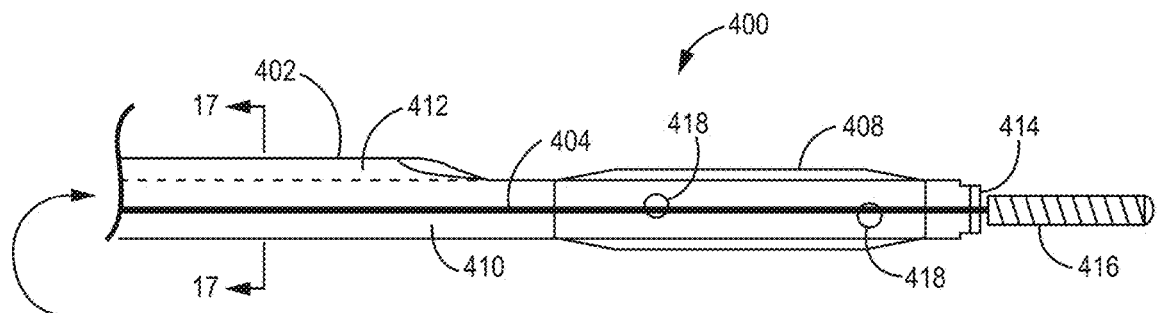
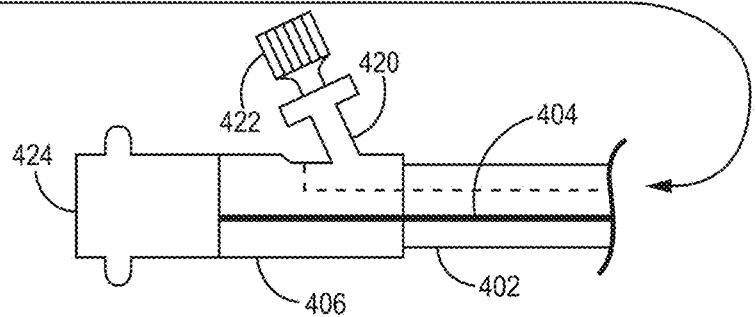
FIG. 16

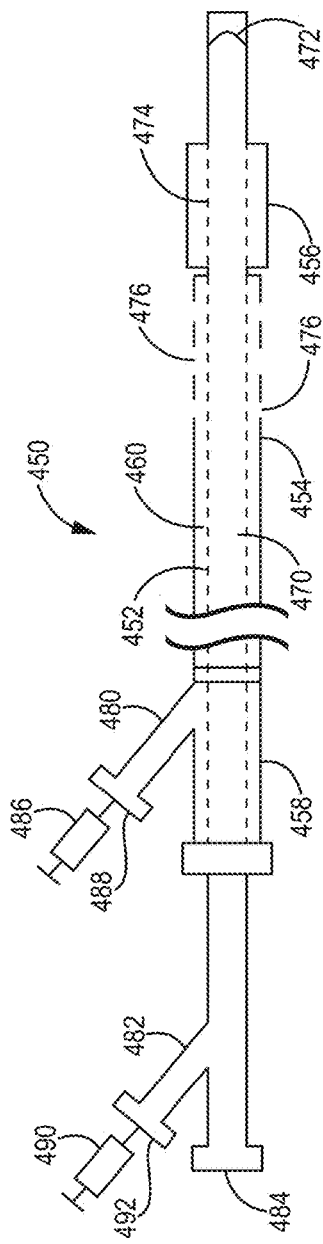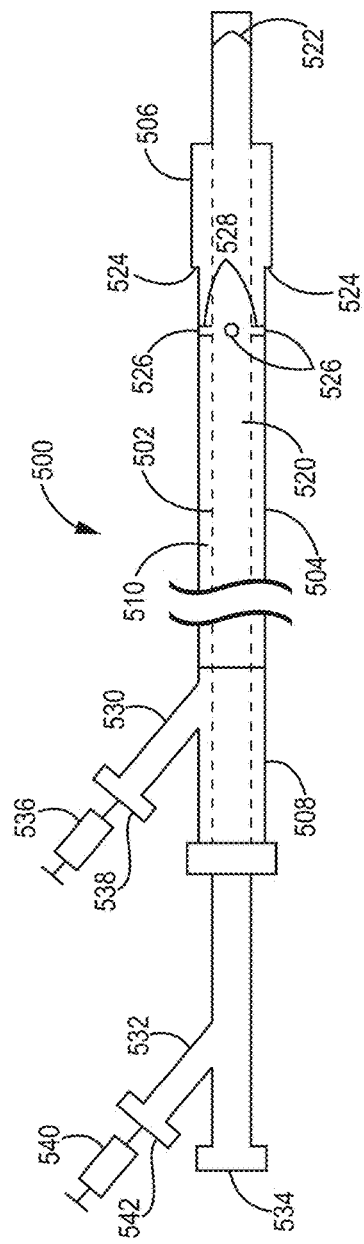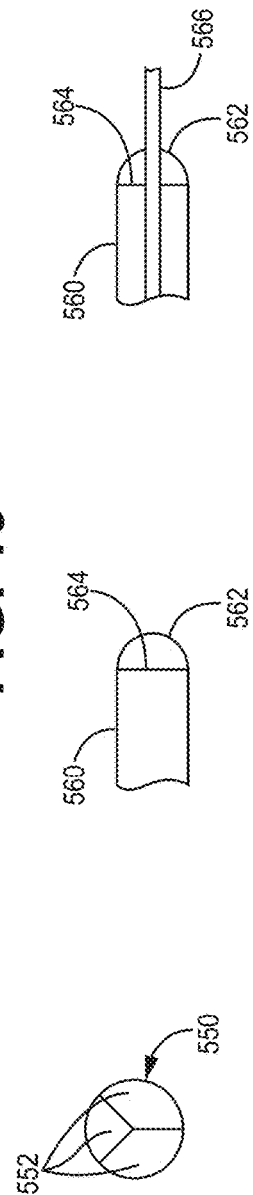

HYDRAULIC DISPLACEMENT AND REMOVAL OF THROMBUS CLOTS, AND CATHETERS FOR PERFORMING HYDRAULIC DISPLACEMENT

CROSS REFERENCE TO RELATED APPLICATIONS

This application claims priority to U.S. provisional patent application 62/404,918 to Ogle filed Oct. 6, 2016, entitled "Hydraulic Displacement and Removal of Thrombus Clot," incorporated herein by reference.

FIELD OF THE INVENTION

The application relates to procedures to facilitate suctioning clots from a vessel through the use of fluidic forces. The application further relates to catheters designed for delivery into narrow blood vessels while allowing blockage of a vessel with proximal fluid infusion to generate fluidic forces to facilitate clot removal.

BACKGROUND OF THE INVENTION

Ischemic strokes can be caused by clots within a cerebral artery. The clots block blood flow, and the blocked blood flow can deprive brain tissue of its blood supply. The clots can be thrombus that forms locally or an embolus that migrated from another location to the place of vessel obstruction, which in either case can be referred to as thrombus clot while obstructing the vessel. To reduce the effects of the cut off in blood supply to the tissue, time is a significant factor, and it can be desirable to restore blood flow in a reduced period of time. The cerebral artery system is a highly branched system of blood vessels, which provide blood to the brain and are connected downstream to the interior carotid arteries. The cerebral arteries can be very circuitous. Medical treatment devices should be able to navigate along the circuitous route posed by the cerebral arteries for placement into the cerebral arteries.

SUMMARY OF THE INVENTION

In a first aspect, the invention pertains to a method for removing a clot from a patient's vessel, the method comprising:
 occluding the vessel with an occluding element distal to the clot;
 infusing liquid between the clot and the occluding element; and
 aspirating liquid from the vessel proximal to the clot with at least some temporal overlap of infusing and aspirating to induce hydraulic forces against the clot.

In a further aspect, the invention pertains to a catheter comprising a tubular shaft comprising a central lumen and a distal end, a proximal fitting, a balloon having a proximal end and an interior. Generally, the balloon is attached at or near the distal end of the tubular shaft, and the interior of the balloon is in fluid communication with the central lumen. In some embodiments, the tubular shaft comprises one or more infusion ports proximal to the balloon within about 5 centimeters from the proximal end of the balloon.

In another aspect, the invention pertains to a catheter comprising a shaft comprising a tubular element and proximal fittings, the tubular element having a distal end, a first lumen and a second lumen, and not having a distinct guidewire lumen; and a balloon having a proximal end and an interior secured to the outer surface of the shaft at or near the distal end of the shaft in which the interior of the balloon is in fluid communication with the first lumen. In some embodiments, the shaft comprises infusion ports proximal to the distal end of the balloon and within about 5 centimeters of the proximal end of the balloon. The infusion ports can be in fluid communication with the second lumen, and the shaft can be free of infusion ports distal to the balloon and of additional balloons. Furthermore, proximal fittings can comprise a Y-branch fitting providing a first connector for attachment of an infusion fluid source for delivery through the infusion ports and a second connector for attachment of a device configured for delivery and/or removal of balloon expansion fluid.

In additional aspects, the invention pertains to a catheter comprising a balloon, a catheter shaft, and proximal fittings with connections to an inflation fluid source and to an infusion liquid source. In some embodiments, the catheter shaft comprises infusion ports and a dual lumen structure with a guidewire lumen and an auxiliary lumen, and a valve configured to close the distal end of the guidewire lumen when a guidewire is absent. The auxiliary lumen can be in fluid communication either with the interior of the balloon and the connection to the inflation fluid source, or with the infusion ports and the infusion liquid source.

BRIEF DESCRIPTION OF THE DRAWINGS

FIG. 1 is a side view of a treatment system with a microcatheter adapted for infusion riding over a fixed wire single lumen balloon catheter.

FIG. 2 is a sectional view of the system of FIG. 1 taken along line 2-2 of FIG. 1.

FIG. 3 is a side view of a single lumen balloon/infusion catheter with an integral distal coil.

FIG. 4 is sectional view of the single lumen balloon/infusion catheter of FIG. 3 taken along line 4-4 of FIG. 3.

FIG. 5 is a fragmentary view of infusions ports for the balloon/infusion catheter of FIG. 3 covered with an elastomer valve.

FIG. 6 is a side view of a single lumen balloon/infusion catheter with a fixed internal wire and an integral distal coil.

FIG. 7 is a sectional view of the single lumen balloon/infusion catheter of FIG. 6 taken along line 7-7 showing a proximal securing structure for the fixed wire.

FIG. 8 is a side view of a single lumen balloon/infusion catheter riding over a guide structure with a valve/seal near the distal end of the catheter engaging a wire of the guide structure, in which a balloon/insert depicts a proximal manifold fitting suitable for attachment to the proximal fitting of the catheter.

FIG. 9 is a fragmentary side view of an alternative embodiment of a single lumen balloon/infusion catheter with a fixed wire and a valve over the infusion port(s).

FIG. 10 is a side view of the wire of the single lumen balloon/infusion catheter of FIG. 9 shown separated from the catheter, in which a balloon/insert depicts a rotated view of the proximal end of the wire having a flattened shape.

FIG. 11 is a side view of the catheter of the single lumen balloon/infusion catheter of FIG. 9 separated from the fixed wire.

FIG. 12 is a fragmentary view of the proximal end of the single lumen balloon/infusion catheter of FIG. 9 in which a fitting comprises a tubular receiving element for supporting a floating end of the flattened wire of FIG. 10.

FIG. 13 is a fragmentary side view of an alternative tip of the single lumen balloon/infusion catheter of FIG. 9 in which the optional coil is replaced with a canon the distal end of the wire.

FIG. 14 is a side view of a balloon/infusion catheter with two lumen, an annular infusion port and a fixed wire within the lumen of an inner tubular element.

FIG. 15 is a sectional view of the balloon/infusion catheter of FIG. 14 taken along line 15-15 of FIG. 14 showing crimped portions of an outer tubular element to secure the outer tubular element to an inner tubular element.

FIG. 16 is a side view of a balloon/infusion catheter having a coextruded unitary element with two lumen in which the proximal and distal ends are displaced to allow for showing the structure in more detail while excluding from view a long unchanging section of the shaft.

FIG. 17 is a sectional view of the balloon/infusion catheter of FIG. 16 taken along line 17-17 showing the two lumen and the fixed wire.

FIG. 18 is a side view of a balloon/infusion catheter with two lumens and distal valve/seal to provide for riding of the catheter over a guide structure, in which the guide lumen is combined with the balloon lumen.

FIG. 19 is a side view of a balloon/infusion catheter with two lumens and distal valve/seal to provide for riding of the catheter over a guide structure, in which the guide lumen is combined with the infusion lumen.

FIG. 20 is a front view of an embodiment of a valve/seal for engaging a guide structure, in which the valve/seal comprises three leaflets.

FIG. 21 is a fragmentary side view of an alternative embodiment of a valve/seal for engaging a guide structure with a central hole that seals when a guide structure that closes when a guide structure is not present.

FIG. 22 is a fragmentary side view of the valve/seal of FIG. 21 with a guide structure passing through the valve/seal.

DETAILED DESCRIPTION

Figure 23:
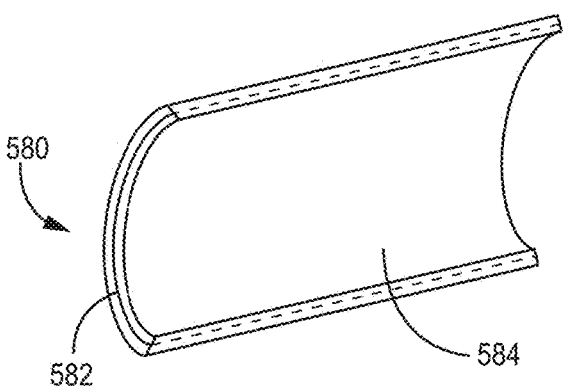
FIG. 23 is a fragmentary perspective view of a section of catheter wall having metal reinforcing wire embedded within a polymer wall.

Devices and corresponding methods are described to effectuate clot removal within an artery using a combination of suction and liquid infusion to loosen the clot with modest forces on the vessel wall. Fluidic forces generated by the flow from the distal infusion relative to the clot position to an aspiration catheter can push the clot in a distal to proximal direction for removal. Generally, a distal balloon or other occlusions device can be extended to occlude the vessel at a position past the clot to direct the infusing liquid back in a proximal direction toward an aspiration catheter.

The use of an infusing liquid can reduce the forces on the vessel generated by the aspiration from the vessel. Therapeutic systems can then comprise a distal occlusion balloon, an infusion device and an aspiration catheter, as well as ancillary devices facilitating the procedure, such as a guidewire, guide catheter, and/or other devices. Single lumen and dual lumen balloon catheters designed for performing the infusion involved in the fluidic assist procedure are described herein. Fluidic based clot removal systems can provide desirable alternatives to other mechanical clot removal systems. The fluidic forces, hydraulic and/or hydrodynamic forces, can tend to dilate the vessel to loosen the clot and prevent significant vessel collapse induced by suction to remove the clot without significantly abrading the vessel wall. These procedures and corresponding devices can be designed for use to address acute ischemic stroke within tortuous cerebral arteries.

Various methods have been developed for removal of clots within arteries, especially in the context of acute stroke. Various clot engagement tools are commercially available and aspiration catheters are also available to facilitate clot removal. The procedures described herein provide an alternative to mechanical engagement of the clot, which can result in fragmentation of the clot and/or abrasion of the blood vessel wall. The procedures also provide an alternative to introduction of aspiration alone that can result in large pressure fluctuations within the vessel that also can injure blood vessel walls or other tissue adjacent the blood vessel. Also, use of aspiration without infusion tends to reduce local blood vessel pressure that can tend to reduce blood vessel diameter that can hinder removal of the clot by collapsing the vessel around the clot. Recently, the use of fluid profusion in conjunction with aspiration to reduce incidence of large pressure drops was described in published U.S. patent application 2017/0056061A1 to Ogle et al. (hereinafter the '061 application), entitled "Thrombectomy Devices and Treatment of Acute Ischemic Stroke With Thrombus Engagement," incorporated herein by reference.

Less invasive procedures, which are commonly referred to in the art as minimally invasive procedures, are desirable in the medical context to reduce patient recovery times and hopefully to improve outcomes when appropriate. In particular, less invasive procedures are commonly performed in the vasculature using catheter based system for reaching remote locations in a selected blood vessel for the performance of various treatment processes. These procedures can also be referred to as percutaneous procedures or transluminal procedures, in contrast with open surgical procedures, to emphasize the delivery through a vessel lumen. The discussion herein focuses on treatment of ischemic stroke since the devices can be particularly effective to treat these clinically important conditions, although the devices can be used in other procedures both in the vasculature and other bodily vessels. Patients include humans and can include other mammals, such as pet animals and farm animals. The terms proximal and distal are used in their conventional sense in the art, i.e., proximal refers to closer to the point of entry into the patient along the path in the vasculature or other vessel and distal refers to farther from the point of entry along the path in the vasculature.

For the treatment of strokes, the treatment devices are advanced through arteries to blood vessels of the brain. Blood vessels generally relevant for acute stroke treatment are downstream in the blood flow from the internal carotid arteries, and arteries generally branch and decrease in average diameter as the vessel proceeds in a downstream direction in the arterial vasculature. The body has a right internal carotid artery and a left internal carotid artery. For convenience, the blood vessels downstream from the internal carotid arteries are referred to herein as cerebral arteries. The cerebral arteries can be accessed with catheter based systems from, for example, a femoral artery in the groin, an artery in the arm, or the carotid artery in the neck using hemostatic procedures and appropriate fittings, such as those known in the art. The cerebral arteries are known to follow circuitous paths, and complications in tracking devices along the vessels also follows due to shrinkage in diameter and branching of the vessels in a distal direction from the carotid artery as well as potentially dangerous conditions from damage to the blood vessel. It can be desirable to access tortuous narrow arteries for stroke treatment. The devices described herein are designed for advantageous use in these tortuous narrow cerebral vessels, but a person of ordinary skill in the art will recognize utility of these devices in other medical procedures.

As described herein, the fluidic aspects of the process are further accentuated through the distal occlusion of the vessel combined with distal profusion of the vessel to provide for establishment of a flow from a position distal to the clot to a proximally positioned opening into an aspiration catheter to facilitate dislodging and removal of the clot using hydraulic forces. In some embodiments, a microcatheter in combination with an appropriately small balloon catheter can be used to perform the procedure in which fluid is infused between the microcatheter and the balloon catheter body. Specifically designed devices can be advantageously used to perform the procedure and can be based on a single lumen or a dual lumen. In single lumen catheter embodiments, the catheter can have no associated wire, an integral wire to provide desired mechanical performance, or the catheter can ride over a distinct guidewire with a structure (seal and/or valve) to inhibit flow from the lumen distal to the balloon. The single lumen functions for both infusion and balloon inflation. In dual lumen devices, again a wire can be integral or distinct with appropriate flow restricting structures. Separate lumen can be used for balloon inflation and infusion of liquid, and for appropriate embodiments a guidewire lumen can be combined with either the balloon lumen or the infusion lumen. While a non-balloon occlusion device can be used the perform the hydraulic assisted procedures described herein, the discussion herein focuses on balloon structures, which can provide desired performance in the procedures described herein and straightforward disengagement for removal.

The basic aspects of the procedures described herein involve placement of an occlusion balloon distal to the clot, an infusion port between the occlusion balloon and the clot, and an aspiration catheter with the suction opening proximal to the clot. The occlusion balloon can be compliant, i.e., formed of an elastic material, to occlude the vessel with modest forces on the vessel walls. Suitable guidewires, microcatheters and aspiration catheters for use in the neurovasculature are described below and are also described in detail in published U.S. patent application 2016/0199620 to Pokorney et al., entitled "Medical Guidewires for Tortuous Vessels," incorporated herein by reference and the '202 application. Commercial compliant balloon approved for the neurovasculature include, for example, TransForm® (Stryker Neurovascular), Specter C or XC® (Microvention/Terumo), Hyperform™ (Covidien), or Ascent® (DePuy Synthes/Codman Neurovascular). However, these balloons have a greater diameter than desirable for the procedures described herein for many vessels. Smaller profile balloons can be provided with the desired functionality using similar designs with correspondingly smaller components. Guidewires and in some embodiments microcatheters can provide for access to the vessel distal to the clot and maintenance of access to the region distal to the clot for placement of the balloon/infusion catheter appropriately positions distal to the clot.

The infusion of liquid along with aspiration can generate a flow of liquid from distal to proximal of the clot with the corresponding generation of hydraulic forces and/or hydrodynamic forces. For convenience, herein the forces generated in the procedures are referred to as hydraulic forces, which may in some sense can include hydraulic forces, hydrodynamic forces or a combination thereof. Either by initiating the infusion prior to the aspiration and/or by controlling the various flow rates, the local pressure in the vessel may increase somewhat, and such a modest increase in pressure can flex the vessel wall to potentially loosen the grip of the vessel wall on the clot. Thus, both the balloon expansion and the control of the pressures can work to loosen the clot to facilitate removal of the clot. The forces on the vessel wall should be controlled to avoid injury to the vessel wall. The distal to proximal liquid flow correspondingly applies distal to proximal forces on the clot to tend to move the clot toward the aspiration catheter. The objective is to dislodge the clot so that it can be taken up by the aspiration catheter or to bring the clot to the aspiration opening for removal from the patient with the catheter.

The procedure can be practiced with a treatment system assembled from a balloon catheter, an infusion catheter (which can be combined into a single device with the balloon catheter), an aspiration catheter, and optionally other devices suitable for the neuro-vasculature or other corresponding vessel. For use in the neuro-vasculature, it is generally desirable to use an independent guidewire to facilitate reaching more remote sites in the vessel, although a guidewire may be removed once additional components are delivered near the treatment site. To guide the procedures, generally, a guide catheter is placed in the carotid arteries, e.g., an internal carotid artery or a common carotid artery, through which additional devices can be guided to smaller vessels downstream. The guide catheter can comprise a hemostatic valve for the introduction of additional devices. In some embodiments, the guide catheter can also have an occlusion balloon that can be actuated to close off flow past the balloon. It can be desirable to stop flow for at least a part of the procedure. Also, aspiration can optionally be applied through the guide catheter as an alternative to or in addition to use of a separate aspiration catheter or in addition.

While existing devices can be used at least in some vessels to implement some of the procedures described herein, desirable device designs are described that provide advantages with respect to implementation simplification as well as design of the devices to provide the desired hydrodynamic flow. The new devices described herein have a common feature of infusion ports positioned proximal along the shaft relative to a balloon. Some embodiments of the catheter have a single lumen for both the infusion liquid and for the balloon expansion. Other embodiments of the catheter have two lumen with separate lumen for balloon inflation and deflation, and for infusion. A catheter design with a single lumen generally involves a simpler structure with the potential for a smaller diameter with comparable construction materials. A catheter design with a dual lumen provides for additional ability to use different fluid pressures for infusion relative to the balloon inflation pressures as well as for adjusting the volume of delivered fluid for infusion. The catheter designs can have no associated wire structure, or can have an integral wire to control flexibility and maneuverability of the catheter, or can ride over a separate guide structure, e.g., guidewire, using a flow control structure to maintain liquid in the catheter such that a guidewire lumen can serve dual roles. Catheter embodiments that share a guidewire lumen with another functional lumen can make more efficient use of lumen volume to facilitate achieving a desired device size.

For use in the neurovasculature, the small diameter of the vessels generally provides a significant constraint of the devices. When delivering a plurality of coaxial devices, the available lumen dimensions of the outer devices is effectively constrained by the obstructed space occupied by the internal devices. Thus, it can be desirable to design special purpose devices to implement the improved procedures described herein such that the limited lumen volume can be used more effectively. An occlusion balloon catheter with infusion capability is described in Published U.S. patent application 2013/0245552 to Ogle et al., entitled "Vascular Medical Devices with Sealing Elements and Procedures for the Treatment of Isolated Vessel Sections," incorporated herein by reference. However, the device in the '552 application is intended for use in large vessels and is not designed for fitting into narrow vessels such as portions of the neurovasculature. The introduction of a separate guidewire lumen would consume a significant amount of the internal space of the device for the walls to form the separate lumen, and the loss of internal volume correspondingly limits the available size of a separate profusion or infusion lumen.

In specific catheter embodiments herein, the balloon lumen can be combined with the guidewire lumen. If a guide structure is left in place, the guidewire itself can function as a closure to reduce, to a reasonably small value, or eliminate exchange of blood flow into the balloon during delivery of the catheter and liquid out from the lumen when the balloon is inflated. A catheter with a guidewire lumen shared with a balloon lumen with a valve to close the guidewire lumen is described in U.S. Pat. No. 6,306,124 to Jones et al., entitled "Microcatheter," incorporated herein by reference. The '124 patent described balloon catheters with very small diameters down to sub-millimeter. The presence of a flow control structure, such as a valve or diaphragm, can allow removal of a guidewire while closing off the flow into the corresponding lumen.

The use of suction alone has provided encouraging results for the treatment of acute ischemic stroke. Alternative devices are available to mechanically dislodge clots resulting in strokes, and these devices can be termed stent retrievers, although some of these devices are not quite derivatives of stents. Suction can also be used with stent retrievers or the like to provide the combined efficacies of the approaches. Furthermore, suction, while potentially very effective, the degree of suction provided for effective clot removal can deplete sections of the vessel of blood resulting in significant collapsing forces on the vessel and corresponding forces on adjacent tissue, which may be undesirable in some cases. While suction can be effective to dislodge and remove the clots, collapse of the vessel around the clot due to liquid removal may not facilitate the process and may increase the corresponding forces. The hydraulic/hydrodynamic forces described herein generate forces on both sides of the clot tending to remove the clot while potentially tending to dilate the vessel to also loosen the clot. Thus, the procedures can be designed to reduce the force extremes within the vessel and on the surrounding tissue while potentially being even more effective to remove clots.

Aspiration catheters or suction catheters are available to provide the suction for the hydraulic assisted procedures described herein, and these catheters are described in detail below. Aspiration catheters can be effectively used along with the catheter(s) to provide occlusion and infusion and optionally along with additional treatment devices, such as mechanical devices to engage clots and/or filter style devices that can capture loose emboli as well as optionally engaging the clot with a more cushioned element to limit forces on the vessel wall. Various systems for clot treatment are described below. Whether used to provide the hydraulic treatment alone or used in combination with additional treatment or protection devices, the hydraulic treatment procedures described herein provide important tools with the possibility to provide more gentle removal of clots from vessels that can be particularly effective for the alleviation of acute ischemic stroke conditions.

Catheters for Providing Occlusion and Infusion

Specific catheter structures are described for providing occlusion of distal flow, e.g., with a balloon, and proximal liquid delivery to generate desired hydraulic forces in the vessel against a clot in a distal to proximal direction. The common features of the devices are an occlusive element and infusion ports, which can be configured in various configurations. The catheters are intended for use with aspiration catheters and optionally other devices to facilitate use of the catheter(s) and/or to supplement the treatment of the vessel, and systems of devices and procedures are discussed in the following sections. To perform the occlusion and infusion functions, the catheters can comprise one or two lumens, and in general do not have additional lumen extending from near the distal end of the catheter to the proximal end of the catheter. To provide desired mechanical properties to the catheter, the catheter can comprise an integral wire or the catheter can be designed to ride over a guidewire with a flow control structure to isolate the guidewire lumen from the vessel liquids. Balloon catheters with the ability to also provide infusion can be referred to as balloon/infusion catheters for convenience.

Referring to FIG. 1, catheter system 100 comprises a fixed wire single lumen occlusion balloon catheter 102 (hereinafter balloon catheter 102) and a microcatheter 104. As shown in FIG. 1, balloon catheter 102 is configured for delivery through microcatheter 104. Balloon catheter 102 comprises a spring tip 110, tubular shaft 112 forming lumen 114 with spring tip 110 extending from the distal end of tubular shaft 112, balloon 116, fixed wire 118 fixed within lumen 114, and a proximal fitting 120. Balloon 116 can be a compliant balloon and has an interior in fluid communication with lumen 114 such that adjustment of fluid pressure within lumen 114 can expand or deflate balloon 116. Fixed wire 118 internal to the catheter can provide characteristics similar to a guidewire for the catheter, and spring tip 110 can be optional as long as the catheter tip is configured to avoid injury to the vessel wall. FIG. 2 shows a cross section with the various positions of the components. Delivering balloon catheter 102 through microcatheter 104 can facilitate maneuvering the distal tip of the balloon catheter into a narrow tortuous vessel.

Microcatheter 104 comprises a tubular shaft 130 and proximal fitting 132. Tubular shaft 130 generally can be designed to have an inner diameter sufficiently larger than the outer diameter of tubular shaft 112 of balloon catheter 102 that balloon catheter 102 can move within microcatheter 104 and that infusion liquid can be delivered through space 134 between tubular shaft 130 and tubular shaft 112. Suitable ranges of catheter dimensions is provided below. The delivery of infusion fluid 136 is marked schematically on FIG. 1. In general, suitable fittings are known in the art for fittings 120, 132. In particular, fittings 120, 132 can be Luer fittings, such as female Luer fittings, Tuohy-Borst connectors, or the like. Luer connectors or Tuohy-Borst connectors can be useful for attachment of standard or proprietary fittings or manifold, such as Y-branch fittings or the like to provide desired access to the lumen.

While the combined device in FIG. 1 involves two separate components, in a sense the combined device provides two distinct lumen with one lumen for infusion and a second lumen functioning as a balloon lumen. Single lumen catheter embodiments can provide balloon inflation/deflation along with associated infusion using a common lumen. Three embodiments of single lumen balloon/infusion catheters are shown in FIGS. 3-8, respectively with no wire, a fixed wire or an independent guidewire.

Referring to FIG. 3, an embodiment of a balloon/infusion catheter 150 is shown without a wire such that the catheter body provides the mechanical properties of the catheter. Balloon/infusion catheter 150 comprises tubular shaft 152, optional coil tip 154 extending distally from tubular shaft 152, balloon 156 and proximal fitting 158 at the proximal end of tubular shaft 152. General details of the materials and dimensions of the components are provide below. Tubular shaft 152 comprises a lumen 160 extending from proximal fitting 158 to balloon 156. Lumen 160 generally is blocked at its distal end at or near coil tip 154. If coil tip 154 is not present, the distal end of the catheter can be shaped to avoid damage to the vessel wall. An appropriate opening(s) 162 provides fluid communication between lumen 160 and the interior of balloon 156. Referring to one embodiment shown in cross section in FIG. 4, four openings 164 distributed around the circumference of tubular shaft 152 provide fluid communication between lumen 160 and the interior of balloon 156. Balloon 156 can be sealed around two sections of the shaft (one section proximal and one section distal) to define an interior 166 and an exterior 168 of the balloon in which the balloon interior is isolated from the exterior fluid environment.

One or more infusion port(s) 170 provide for infusion of liquid from lumen 160 delivered from a liquid source attached to proximal fitting 158 into the patient's vessel. Flow of liquid out from lumen 160 tends to lower the pressure within the lumen. Liquid pressure within lumen 160 also provides for inflation of balloon 156. The hydrodynamics should be balanced so that appropriate pressures to maintain the inflated balloon while correspondingly to provide for a desired infusion flow rate. Infusion port(s) 170 can be designed accordingly, and infusion port(s) 170 are also in appropriate proximity to balloon 156 to facilitate placement distal to the clot within tortuous vessels. In particular, the size and number of infusion port(s) 170 can be selected to provide appropriate infusion at pressures inflating balloon 156. In some embodiments, the farthest edge of an infusion port is no more than 5 centimeters from the closest edge of the balloon, and in further embodiments no more than 2.5 centimeters, and this spacing is general for all of the catheter embodiments in this section. A person of ordinary skill in the art will recognize that additional values of infusion port spacing within the explicit ranges above are contemplated and are within the present disclosure.

Also, an embodiment of the infusion structure is shown in FIG. 5 in which an elastic cover 172 covers infusion ports 170. Elastic cover 172 can provide an added measure of control over the infusion process in which a certain amount of pressure may be applied to expand elastic cover 172 to provide for infusion. Elastic cover 172 can be sealed along one edge to tubular shaft 152 and open at an opposite edge to provide for the infusion. Arrows in FIG. 5 are shown to schematically illustrate infusion through the un-sealed edge. Elastic cover 172 can be made from the same or similar material as balloon, 156, although as long as elastic cover 172 provides desired elastic properties, it can be made from a distinct material.

An alternative embodiment of a balloon/infusion catheter 180 with a single lumen is shown in FIG. 6. Balloon/infusion catheter 180 comprises tubular shaft 182, optional coil tip 184 extending distally from tubular shaft 182, balloon 186, fixed wire 188, and proximal fitting 190 at the proximal end of tubular shaft 182. General details of the materials and dimensions of the components are provided below. Balloon/infusion catheter 180 is similar in structure to balloon/infusion catheter 150 except for the inclusion of fixed wire 188. Tubular shaft 182 comprises lumen 192, opening(s) 194 providing a fluid connection between lumen 192 and the interior of balloon 186, and infusion port(s) 196 to provide liquid flow out from lumen 192. The features of opening(s) 194 and infusion port(s) 196 can correspond with the features described above in the context of FIG. 3 for corresponding opening(s) 162 and infusion port(s) 170 including but not limited to the alternative embodiments of FIGS. 4 and 5. Fixed wire 188 can be secured within lumen 192 at or near its respective ends. Referring to FIG. 6, distal end 198 of fixed wire 188 can be secured in a structure terminating lumen 192 and fastening coil tip 184 or alternative tip, and such structure can comprise, for example, an adhesive plug or the like, possibly further secured with a radiopaque band 200 or the like. A clip or scaffold 202 can be secured within lumen 192 to support fixed wire 188. An alternative embodiment with a floating wire proximal end is described below. Scaffold 202 can have any reasonable structure providing for liquid flow past the scaffold within lumen 192. Referring to FIG. 7, scaffold is shown with arms 204 holding fixed wire 188 in place.

An embodiment of a balloon/infusion catheter 210 with a single lumen that rides over a guide structure 212, such as a guidewire, is shown in FIG. 8. Balloon/infusion catheter 210 comprises tubular shaft 214, optional coil tip 216 extending distally from tubular shaft 214, balloon 218, and proximal fitting 220 at the proximal end of tubular shaft 214. General details of the materials and dimensions of the components are provided below. Balloon/infusion catheter 210 is similar in structure to balloon/infusion catheter 150 except for structure to accommodate interfacing with guide structure 212. Tubular shaft 214 comprises lumen 222, opening(s) 224 providing a fluid connection between lumen 222 and the interior of balloon 218, and infusion port(s) 226 to provide liquid flow out from lumen 222. The features of opening(s) 224 and infusion port(s) 226 can correspond with the features described above in the context of FIG. 3 for corresponding opening(s) 162 and infusion port(s) 170 including but not limited to the alternative embodiments of FIGS. 4 and 5. Guide structure 212 can be a guidewire or other structures such as a wire based filter structure, and suitable guide structures are described further below. Tubular shaft 214 can comprise a flow control structure 228 to provide for movement of tubular shaft 214 relative to guide structure 212 with little or no liquid exchange from lumen 222 into or out from the distal end of tubular shaft 214. Suitable structures for flow control structure 228 are described further below. Proximal fitting 220 can have a female Luer connector a Tuohy-Borst connector or the like for attachment to additional fitting components, such as the Y-branched manifold 230 shown in the balloon of FIG. 8. Y-branch manifold 230 comprises a male Luer connector 232, side arm 234 with a connector 236, such as a Luer connector, for attachment to a liquid source and a hemostatic valve 238 that provides for relative movement of catheter 210 and guide structure 212 with little or no blood loss when the distal portion of the devices are in a patient's vessel, although other fitting configurations can be used as would be recognized by a person of ordinary skill in the art.

A specific embodiment of a balloon/infusion catheter 250 with a single lumen and a fixed wire is shown in FIGS. 9-11. Specifically, FIG. 9 shows the assembled structure while FIG. 10 shows the separate wire and FIG. 11 shows the separate catheter. Referring to FIG. 9, balloon/infusion catheter 250 comprises catheter body 252 and fixed wire 254. A shown in FIGS. 9 and 11, catheter body 252 comprises a distal segment 256, taper segment 258 and proximal segment 260. Distal segment 256 and proximal segment 260 has approximately constant diameters while taper segment 258 transitions between the diameters of distal segment 256 and proximal segment 260. Taper segment 258 can have a roughly linear taper or other reasonable curved taper. Distal segment 256 comprises an infusion port 262 and two openings 264 to provide for liquid flow into and out from balloon 266. Balloon 266 is sealed along two edges to distal segment 256 to isolate the interior of balloon 266. Elastic cover 268 covers infusion port 262 to function as a valve that opens to allow for infusion at a sufficient pressure in lumen 270 within the interior of catheter body 252.

Referring to FIGS. 9 and 10, fixed wire 254 comprises a proximal section 280, seven sequentially tapered sections 282, 283, 284, 285, 286, 287, 288, and distal coil 290. While FIGS. 9 and 10 depict a fixed wire with many sequentially tapered sections, a fewer number of tapered sections can be used, such as one, two, three, four, five or six, and if desired a greater number of tapered sections can be used. Sections of fixed wire 254 can have approximately discontinuous diameter changes or a desired wire taper connecting adjacent sections of tapered sections 282-288. A plug 292, such as an adhesive plug or a polymer plug, can be located at the proximal end of distal coil 290 to help secure fixed wire 254 to catheter body 252 to isolate a lumen within catheter body 252. Referring to FIG. 9, distal coil 290 can have a capped tip 294. An alternative embodiment is shown in FIG. 13 in which a fixed wire 320 is secured with plug 292 and fixed wire 320 terminates with a blunt tip 322 without a coil while avoiding injury to the vessel wall.

In the embodiment of FIG. 10, the distal end 300 of fixed wire 254 is flattened, as shown in the insert perpendicular to the continuous view. Referring to FIGS. 11 and 12, the proximal end of catheter body 252 can comprise proximal fitting 302 that comprises an oblong receiving tube 304 within body portion 306 and a Tuohy-Borst connector or other suitable connector 308. Oblong receiving tube 304 is shaped to receive flattened distal end 300 that floats in the sense of not rigidly secured in a direction along its length. Body portion 306 can be used for gripping the device and manipulation by a user to rotate and slide balloon/infusion catheter 250 as appropriate. Proximal fitting 302 can be secured to catheter body 252, for example, using suitable approaches such as heat bonding, adhesive bonding, molding, a combination thereof, or the like.

For use in the neurovasculature, appropriate ranges of dimensions of components of a balloon/infusion catheter can be specified. The following dimensions specifically refer to the embodiments of balloon/infusion catheter of FIGS. 9-12, but the values can also be applicable to the embodiments of FIGS. 1-8. The length of catheter body 252 can be from 150 cm to 250 cm and a particular embodiment can have a length of 185 cm±1 cm. Distal segment 256 can have a length from about 15 cm to about 50 cm with a particular value of 23 cm, and the taper segment can have a length from about 15 cm to about 3 cm with a particular value of about 7 cm. Catheter body 252 can have a wall thickness (materials and processing describe further below) from about 0.0015 inch (in) to about 0.0035 in, with a particular embodiment being 0.0025 in, so that the inner diameter is about 0.005 in less than the outer diameter (twice the wall thickness). The proximal outer diameter can be from about 0.025 in to about 0.015 in with a particular embodiment having a value of 0.019 in, and the distal outer diameter can be from about 0.020 in to about 0.012 in with a particular value of 0.015 in. The inner diameters follow from the outer diameters and wall thicknesses. A person of ordinary skill in the art will recognize that additional ranges within the explicit ranges above are contemplated and are within the present disclosure.

Fixed wire 254 can extend past the distal end of catheter body 252, such as with at least part or all of distal coil 290 extending over a portion of fixed wire 254 projecting past plug 292. The portion of fixed wire 254 extending past the end of catheter body 252 suggests a longer fixed wire relative to catheter body 252. On the proximal side, fixed wire 254 may terminate before the proximal end of catheter body 252, such as shown in the embodiment of FIG. 6, but in the embodiment shown in FIG. 12, fixed wire 254 extends past the proximal end of catheter body 252. Thus, as shown in FIG. 8-12, fixed wire 254 generally has a length somewhat greater than catheter body 252. The proximal end of fixed wire 254 can have a diameter from about 0.007 in to about 0.012 in, and in some embodiments about 0.009 in. A distal most tapered section can have a diameter from about 0.0025 in to about 0.06 in, and in some embodiments about 0.004 in. The tapered portion of fixed wire 254, i.e., the portion extending in a distal direction from proximal section 280 can have a total length, not including any portion extending under distal coil 290, from about 25 cm to about 70 cm, which can include multiple segments with differing diameters. Along the length of the balloon/infusion catheter 250, the difference between the fixed wire diameter and the catheter inner diameter provides a gap for liquid flow that provides both control of balloon inflation and infusion. The gap may not be constant over the length. The gap along the proximal section of fixed wire 254 can be from about 0.003 in and about 0.007 in, and in some embodiments the proximal gap can be about 0.005 in. The gap at the distal most section of fixed wire 254 can be from about 0.005 in to about 0.0089 in, and in some embodiments about 0.007 in. Balloon 266 and infusion ports 262 can be located along the section of the distal fixed wire, and a larger gap can be desirable in view of the flows in this region. An intermediate region along the length of the catheter can have a narrowed gap. A person of ordinary skill in the art will recognize that additional ranges of lengths diameters and gaps within the explicit ranges above are contemplated and are within the present disclosure.

Several embodiments of two lumen balloon/infusion catheters are shown in FIGS. 14-22. These catheters have the common feature of having only two lumen, and not a third lumen and the designs provide infusion proximal to the balloon and no infusion distal to the balloon. Thus, the designs can provide a small diameter device specifically suited for the procedures described herein.

A first two lumen design provides a unitary structure with an axially annular infusion port analogous to the infusion port formed by the separate components in the system of FIG. 1. Referring to FIG. 14, balloon/infusion catheter 350 comprises an inner tubular element 352, outer tubular element 354, optional fixed wire 356, optional distal coil 358, and proximal fitting 360. In use, infusion fluid flows through the gap between the inner diameter of outer tubular element 354 and the outer diameter of inner tubular element 352. As shown in FIG. 14, proximal fitting 360 comprises a Y-branch manifold 362 with a terminal connector 364, and proximal connector 366. Proximal fitting 360 is shown as a particular embodiment as an integral part connecting outer tubular element 354 with inner tubular element 352, but various alternative structures can be used as long as proximal fitting 360 has an appropriate manifold structure and corresponding connectors. Fixed wire 356 can be secured at its distal end with an adhesive plug, polymer plug or the like, and can float at its proximal end using a structure such as shown in FIG. 12 or can be fixed at its proximal end using a clip or the like that provides for the maintenance of flow while securing the fixed wire.

Inner tubular element 352 and outer tubular element 354 can be secured only at proximal fitting 360 so that outer tubular element 354 floats over inner tubular element 352 over most of their length. In other embodiments, inner tubular element 352 can be secured to outer tubular element 354 at one or more locations along the length of the shafts. Attachments securing inner tubular element 352 and outer tubular element 354 should not significantly block flow between the tubes. Referring to FIG. 15, a cross section view of balloon/infusion catheter 350 shows 4 crimps 370 of outer tubular element 354 securing inner tubular element 352. Heat can be used to soften the polymer of outer tubular element 354 to provide for the crimping. Additionally or alternatively, rivets 372 or other suitable fasteners can be used to secure outer tubular element 354 to inner tubular element 352, as shown in FIG. 14. Similarly, clips 374 or the like can be placed at the distal end of outer tubular element 354 to secure the shafts at the infusion opening. Connections between outer tubular element 354 and inner tubular element 352 can be placed at one, two, three or more positions along the length.

An embodiment of a balloon/infusion catheter 400 with a coextruded dual lumen is shown in FIGS. 16-17. Balloon/infusion catheter 400 comprises dual lumen shaft 402, optional wire 404, proximal fitting 406, and balloon 408. Referring to the sectional view in FIG. 17, dual lumen shaft 402 has a balloon lumen 410 that also serves as a wire lumen, and an infusion lumen 412. Balloon lumen 410 can be circular or oval, as shown. Infusion lumen 412 is shown with an arched shape, but the shape of an extruded infusion lumen may be selected from reasonable choices. Polymer can be extruded simultaneously to form dual lumen shaft 402 to which proximal fitting is then attached. Wire 404 can be a fixed wire or a slidable wire, and securing element 414 can be a polymer or adhesive plug or other structure to fix the wire, or a valve, seal, or alternative structure that restricts flow around a moveable wire. Adhesive or polymer plugs are described above in the context of FIGS. 1, 3 and 6, and valves, seals, or other flow control structures are described further in the context of FIGS. 18-22 as follows, and these discussions can be correspondingly relevant for the device of FIGS. 16-17. Wire 404 can have an optional coil 416 at its distal end. Proximal fitting 406 can be secured at the proximal end of dual lumen shaft 402. The interior of balloon 408 is in fluid communication with balloon lumen 410, such as through openings 418, as shown in FIG. 16. Proximal fitting 406 can comprise a Y-branch manifold 420 in fluid communication with infusion lumen 412, and a connector 422 can be located at the end of Y-branch manifold 420. The proximal end of proximal fitting 406 can comprise another connector 424. Proximal fitting 406 can comprise a receiving tube, such as shown in FIG. 12, to support a floating fixed wire, or a clip or other fastener in proximal fitting 406 or in dual lumen shaft 402 can secure a fixed wire, or a slidable wire can extend proximally from connector 424.

Alternative embodiments of dual lumen catheters for delivery over a guidewire without delivery from a microcatheter are described in the context of FIGS. 18-22. Referring to FIG. 18, dual lumen catheter 450 comprises an inner shaft 452, an outer shaft 454, balloon 456, and proximal fitting 458. An infusion lumen 460 is formed within outer shaft 454 around the exterior of inner shaft 452. Inner shaft 452 has a lumen 470 that functions as a balloon lumen and a guide lumen. Inner shaft 452 further comprises valve 472 in lumen 470 near the distal end of inner shaft 452 to restrict liquid flow past valve 472. Generally, a guide structure generally extends the length of dual lumen catheter 450 and extends in a distal direction from the end of the catheter through valve 472, with the valve again limiting liquid passage in either direction through the valve. The guide structure may or may not be removed prior to inflation of the balloon or infusion. A suitable opening(s) 474 provides for fluid flow to and from lumen 470 and the interior of balloon 456. Infusion lumen 460 provides for fluid flow from the catheter at one or more infusion ports 476 such that liquid can be directed from a proximal reservoir to infusion port(s) 476 near the distal end of the catheter just proximal to balloon 456. Valve/seal embodiments are discussed further after the discussion of FIG. 19.

With respect to FIG. 18, proximal fitting 458 comprises two branch conduits 480, 482, and a proximal connector 484. The particular configuration of proximal fitting 458 can be selected appropriately based on various options that can be used to provide the described functionality. In the particular embodiment shown in FIG. 18, an infusion liquid reservoir 486 is connected to branch conduit 480 at connector 488, and a balloon inflation reservoir 490 is connected to branch conduit 482 at connector 492, such that a guide structure can exit dual lumen catheter 450 at proximal connector 484. In an alternative embodiment, a guide structure can exit dual lumen catheter 450 through branch conduit 480 and through connector 492 with a balloon inflation reservoir connected at proximal connector 484.

Referring to FIG. 19, a dual lumen catheter 500 has a similar structure with dual lumen catheter 450 of FIG. 18 with a reversal of the general placement of the infusion lumen and the balloon lumen. Referring to FIG. 19, dual lumen catheter 500 comprises an inner shaft 502, an outer shaft 504, balloon 506, and proximal fitting 508. A balloon lumen 510 is formed within outer shaft 504 around the exterior of inner shaft 502. Inner shaft 502 has a lumen 520 that functions as an infusion lumen and a guide lumen. Inner shaft 502 further comprises valve/seal 522 in lumen 520 near the distal end of inner shaft 502 to restrict liquid flow past valve/seal 522. Generally, a guide structure generally extends the length of dual lumen catheter 500 and extends in a distal direction from the end of the catheter through valve 522, with the valve/seal again limiting liquid passage in either direction through the valve. The guide structure may or may not be removed prior to inflation of the balloon or prior to infusion. A suitable opening(s) 524 provides for fluid flow to and from balloon lumen 510 and the interior of balloon 506, and balloon 506 can be secured around the exterior of inner shaft 502, the exterior of outer shaft 504, or a combination thereof. Lumen 520 provides for fluid flow from the catheter at one or more infusion ports 526 such that liquid can be directed from a proximal reservoir to infusion port(s) 526 near the distal end of the catheter just proximal to balloon 506. One or more conduits 528 connect lumen 520 with one or more infusion ports 526. Conduits can be formed, for example, by little tubes, such as metal tubes, puncturing through the walls to form the desired conduit structure.

Proximal fitting 508 comprises two branch conduits 530, 532, and a proximal connector 534. The particular configuration of proximal fitting 508 can be selected appropriately based on various options that can be used to provide the described functionality. In the particular embodiment shown in FIG. 19, a balloon inflation reservoir 536 is connected to branch conduit 530 at connector 538, and an infusion liquid reservoir 540 is connected to branch conduit 532 at connector 542, such that a guide structure can exit dual lumen catheter 500 at proximal connector 534. In an alternative embodiment, a guide structure can exit dual lumen catheter 500 through branch conduit 532 and through connector 542 with an infusion reservoir connected at proximal connector 534.

The design of the valve/seal structure can depend on the intended use of the device. For example, if the device is simply intended to ride over a guide structure, a valve structure that provides a seal around a moveable wire can provide desired function. If it is intended that the catheter can ride over a guide structure and subsequently removed, a valve structure can be used that seals following removal of the wire as well as providing a seal around the guide when it is in place. During delivery of the catheter over the guidewire, a valve would be open, which can allow for leakage of blood into the balloon. Leakage of blood into a balloon and corresponding complication associated with imaging of the balloon have been described for valve-less devices with a common guidewire lumen and balloon lumen, see published U.S. patent application 2016/0144157 to Gulachenski et al., entitled "Reinforced Balloon Catheter," incorporated herein by reference. Thus, a valve as described herein can be used to reduce or eliminate such leaking.

A valve in these catheters to close off the guidewire lumen can engage the wire to seal the lumen at the valve. Thus, the guidewire can be pushed through the valve, and the guidewire holds the valve open when it is present. If the guide structure is removed, the valve can close to seal the lumen. While valves can be made from various materials, such as polymers (such as elastomers), ceramics, metal or combinations thereof, for these applications with a relatively low cost and suitable performance, the valves can be formed from elastomers, such as polyurethane or polysiloxane. In some embodiments, the valve can comprise two or three coapting leaflets, with a three leaflet valve 550 shown in FIG. 20 having leaflets 552. Valves for guidewires having two or three leaflets are described also in U.S. Pat. No. 6,306,124 to Jones et al., entitled "Microcatheter," incorporated herein by reference.

Other valve/seal designs can be used. Referring to an embodiment of a valve/seal in FIGS. 21 and 22, catheter 560 has a seal 562 formed with a flexible elastomer with a central hole 564 that is closed when a guide structure is missing, as shown in FIG. 21. A guide structure 566 can push through seal 562 to extend through central hole 564, as shown in FIG. 22. Valves/seals of this type are also discussed in U.S. Pat. No. 6,432,091 to Davey, entitled "Valved Over-The- Wire Catheter," incorporated herein by reference. Valve designs to block flow around a sliding guide structure in which the guide structure is not intended to be removed can be similar to the structures in FIGS. 20-22 except that the valve may not completely seal with the guide structure removed, and such structures are also described in U.S. Pat. No. 5,259,839 to Burns, entitled "Balloon Catheter With Guidewire Valve," and U.S. Pat. No. 9,174,025 to Mallaby, entitled "Rapid Exchange Catheters Having a Sealed Guidewire Lumen and Methods of Making the Same," both of which are incorporated herein by reference. If it is desirable to deliver the guidewire into the patient prior to mounting the profusion catheter onto the guidewire, a loading tool can be used to hold the valve open while the guidewire is inserted into the lumen from the distal end. A suitable loading tool can be a slit polymer tubular section that can be inserted past the valve and then peeled away after loading the guidewire.

In general, the catheters shown in FIGS. 1-22 comprise one or more marker bands and/or other imageable components can be used to position the balloon and profusion port(s) distal to the clot. While the structures provide appropriate constraints on the placement of imageable elements based on achieving desired mechanical performance, there generally is significant design flexibility for the placement of such radiopaque elements, and a person of ordinary skill in the art can manage such placement to achieve convenience for the corresponding procedures.

As used herein, guidewire or guide structure can refer to any appropriate elongated element suitable to guide the delivery of the treatment catheter, such as a wire, coil, or integrated guide structure with a core element and an overtube. Specific examples of guide structures are described below.

Catheter components can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates, polysiloxanes (silicones), polycarbonate urethanes (e.g., ChronoFlex AR®)), mixtures thereof, or other suitable biocompatible polymers. Radio-opacity can be achieved with the addition of metal markers, such as platinum-iridium alloy, tantalum, tungsten, gold, platinum-tungsten alloy or mixtures thereof, such as in the form of wire or bands, or through radio-pacifiers, such as barium sulfate, bismuth trioxide, bismuth subcarbonate, powdered tungsten, powdered tantalum or the like, or combinations thereof, added to the polymer resin. Generally, different sections of aspiration catheter can be formed from different materials from other sections, and sections of aspiration catheter can comprise a plurality of materials at different locations and/or at a particular location. In particular, it may be desirable to form seal components from an elastomeric polymer, such as suitable polyurethanes, rubber, synthetic rubbers, polydimethyl siloxane, polytetrafluoroethylene, other elastomers or combinations thereof. In addition, selected sections of the catheter can be formed with materials to introduce desired stiffness/flexibility for the particular section of the catheter. Similarly, fittings can be formed form a suitable material, such as one or more metals and/or one or more polymers.

In some embodiments, a balloon/infusion catheter, microcatheter, guide catheter, suction extension or appropriate portions thereof comprises a thermoplastic polymer with embedded metal elements, which reinforces the polymer. Suitable polymers include, for example, polyamides, i.e., nylons, polyether-amide block copolymers, polyolefins, combinations thereof, or the like. The wire can be braided, coiled or otherwise placed over a polymer tubing liner with some tension to keep the wire in place over the tubing liner. A cutoff portion of a representative reinforced catheter section is shown in FIG. 23, in which catheter section 580 has metal reinforcement 582 embedded in the polymer wall 584. In some embodiments, suction tip can comprise both braided wire and a metal coil, which provide desirable flexibility and resilience to the element as well as mechanical strength with a thin wall. A polymer jacket, such as a heat shrink polymer, can then be placed over the top or the polymer softened to allow incorporation of the metal reinforcements. Upon heating to a temperature over the softening temperature or heat shrink temperature of the polymer and subsequent cooling, the wire becomes embedded within the polymer. In appropriate embodiments, the liner and jacket can be the same or different materials. Suitable wire includes, for example, flat stainless steel wire or the like. Wire diameters can range from about 0.00025 inch (0.00635 mm) to about 0.004 inch (0.1 mm) and in further embodiments from about 0.0005 inch (0.013 mm) to about 0.003 inch (0.075 mm). Braid picks per inch can be from about 20 to about 250 picks per inch and in further embodiments from about 50 to about 150 picks per inch. Coils can be single or multiple filament coils having, for example, pitches from about 0.005 inch (0.13 mm) to about 0.1 inch (2.54 mm) and in further embodiments form about 0.01 inch (0.26 mm) to about 0.050 inch (1.27 mm). A person of ordinary skill in the art will recognize that additional ranges within the explicit ranges below are conceived and are within the present disclosure. The wire adds additional mechanical strength while maintaining appropriate amounts of flexibility. The wire can provide some radio-opacity although radiopaque bands generally would provide a darker and distinguishable image relative to the wire. However, the image of the wire can provide further visualization of the catheter during the procedure.

To decrease the chance of accidental removal of the radiopaque band from the catheter and to decrease the chance of the radiopaque band catching onto other objects within the vessel, a metal reinforcing wire can be used to cover or enclose the radiopaque band with the metal wire subsequently being embedded within the polymer. As described in the previous paragraph, the metal wire can comprise interwoven wires, coil, combinations thereof, or the like. A polymer jacket can be placed over the metal wire, which is correspondingly covering the radiopaque band(s), and the heat bonding embeds the radiopaque marked band also. Placement of the marker band under metal wire can prevent the band from being separated from the catheter in the event that the wall is kinked or collapsed. If collapse or kinking of the catheter wall occurs, the braid-wire over the surface of the band collapses down over the marker band to prevent it from separating from the structure.

Figure 24:
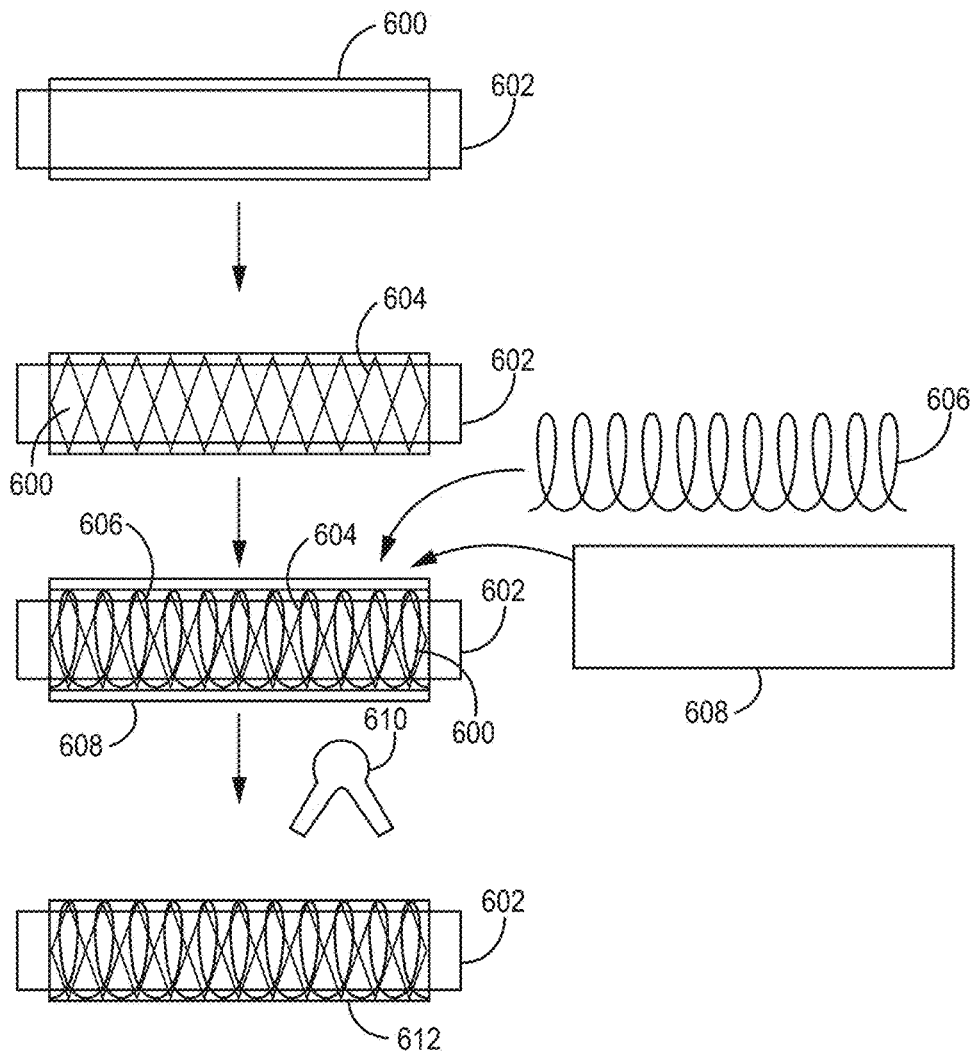
FIG. 24 is a schematic diagram showing processing steps for forming an embodiment of a catheter with embedded metal braiding and/or metal coil within a polymer tubular element.

Referring to FIG. 24, an example of a procedure is shown schematically for forming a section of a reinforced tubular structure for a catheter. Polymer liner 600 is placed over mandrel 602. In the second sequential figure, metal braiding 604 has been placed over the polymer liner, and commercial braiding equipment can be used for this step. As shown in the third figure of the series, a metal coil 606 is placed over braided wire 604 and a polymer cover 608 is placed over the coil 606. A heat source 610 can be used to heat shrink polymer cover 608 to complete the reinforced catheter section 612, as shown in the fourth sequential figure of FIG. 24.

Treatment Systems

Figure 25:
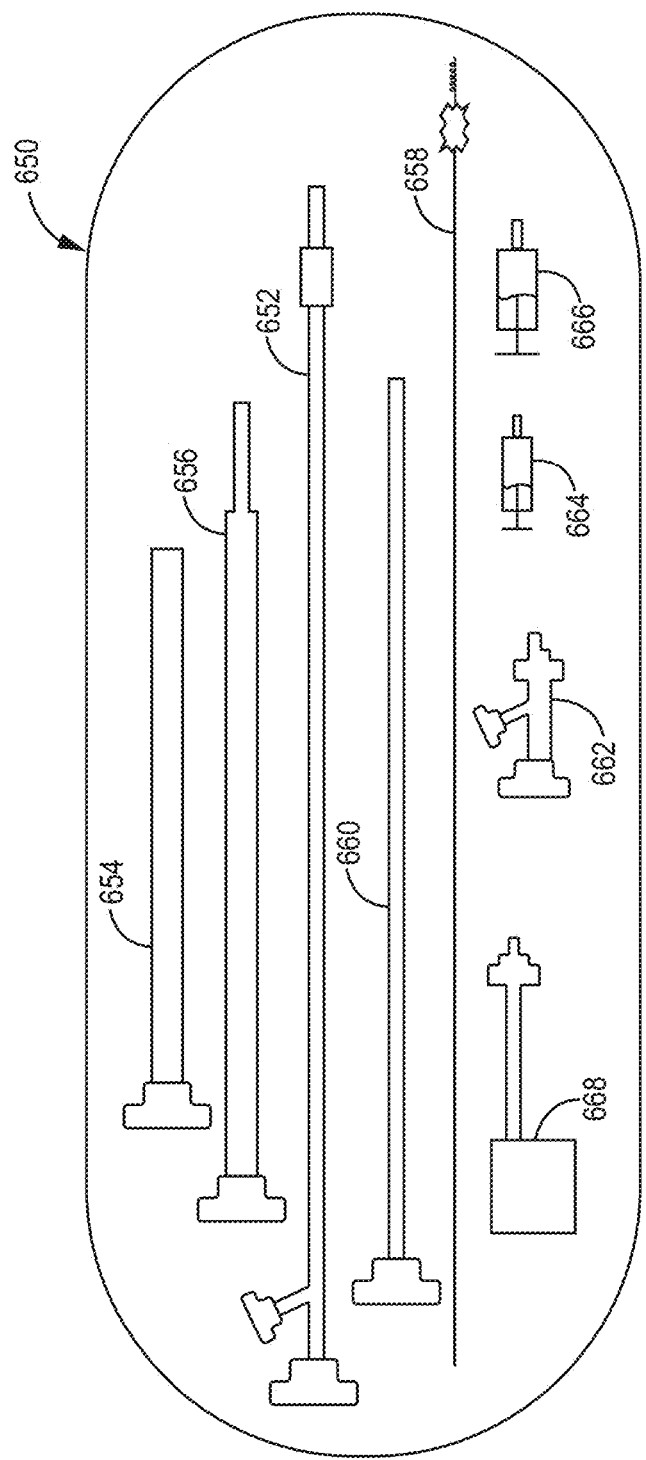
FIG. 25 is a schematic diagram depicting components of a treatment system based on the use of a balloon/infusion catheter with an aspiration catheter useful for the treatment of acute ischemic stroke.

Generally, use of the balloon/infusion catheters described in the previous section also involves the use of an aspiration catheter. A guide catheter generally also is used, which may or may not be a component of an aspiration catheter system. For some procedures, additional components may also be used either simultaneously with the balloon/inflation catheter or sequentially in time. FIG. 25 schematically shows a representative set of devices that can be used in an appropriate combination as a system for the performance of the procedures described herein. Components of a system may or may not be packaged together. Referring to FIG. 25, treatment system 650 comprises balloon/infusion catheter 652, guide catheter 654, aspiration catheter or nozzle 656, guide structure 658, additional treatment structure 660, backend fitting 662, infusion fluid source 664, balloon inflation fluid source 666, and aspiration source 668. A specific treatment system can comprise a subset of these components, additional components of the same type or different type, or a combination thereof, to meet particular therapeutic objectives. In general for embodiments of particular interest, treatment system 650 comprises at least balloon/infusion catheter 652 and aspiration catheter or nozzle 656, in which an aspiration nozzle would function with a guide catheter as an aspiration system. Embodiments of balloon/infusion catheter 652 are described in detail above. While generally any of the embodiments of the balloon/infusion catheters in FIGS. 1-22 can be used, some embodiments may or may not be compatible with all supplemental treatment devices, such as a fixed wire balloon/infusion catheter that generally is not used with a separate guide structure.

Figure 26:
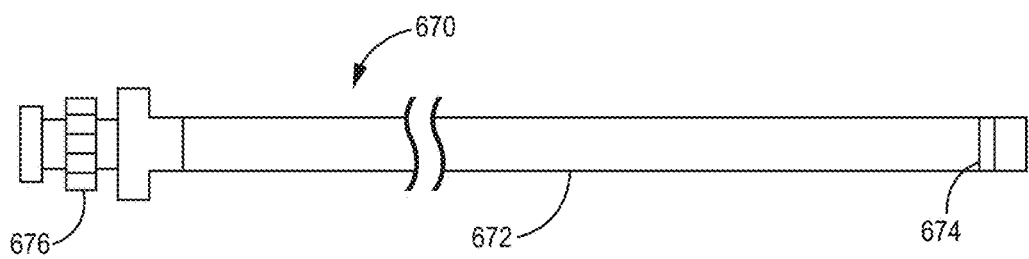
FIG. 26 is a side view of a guide catheter.

A guide catheter 654 can be simply a structure to facilitate delivery of remaining structures into the patient's vasculature, or a guide catheter 654 can function with an aspiration nozzle to form an aspiration system. An embodiment of a guide catheter 670 is shown in FIG. 26, and an embodiment of a guide catheter adapter for use with a suction nozzle is described further below. Referring to FIG. 26, tubular shaft 672 can have an approximately constant diameter along its length, or the guide catheter can have sections with different diameters, generally with a smaller diameter section distal to a larger diameter section. Tubular shaft 672 can have one or more radiopaque marker bands to facilitate positioning of the tubular shaft within the patient, and FIG. 26 depicts a marker band 674 near the distal end of tubular shaft 672, although alternative positions can be used as desired. Tubular shaft 672 can have coatings on the inner surface and/or the outer surface or portions thereof. Also, guide catheter can have a balloon at or near its distal end and a corresponding balloon lumen. Guide catheter 670 can comprise a hemostatic valve 676 at the proximal end of shaft 672 and other fittings can be adapted for use in addition to or as an alternative to hemostatic valve 676, which are connected as a unitary structure or are connected with a suitable connector. The description of catheter materials, dimensions and construction above can be equally applied to the guide catheter.

An aspiration catheter can be an effective component for the removal of cerebral clots, even if used alone. When aspiration catheters are combined with the other elements described herein, the combined treatment systems can offer several elements in the cooperative efforts to remove a clot, although the aspiration catheter may be effective when used alone. The aspiration catheter provides removal forces from the proximal side of the clot.

Figure 27:
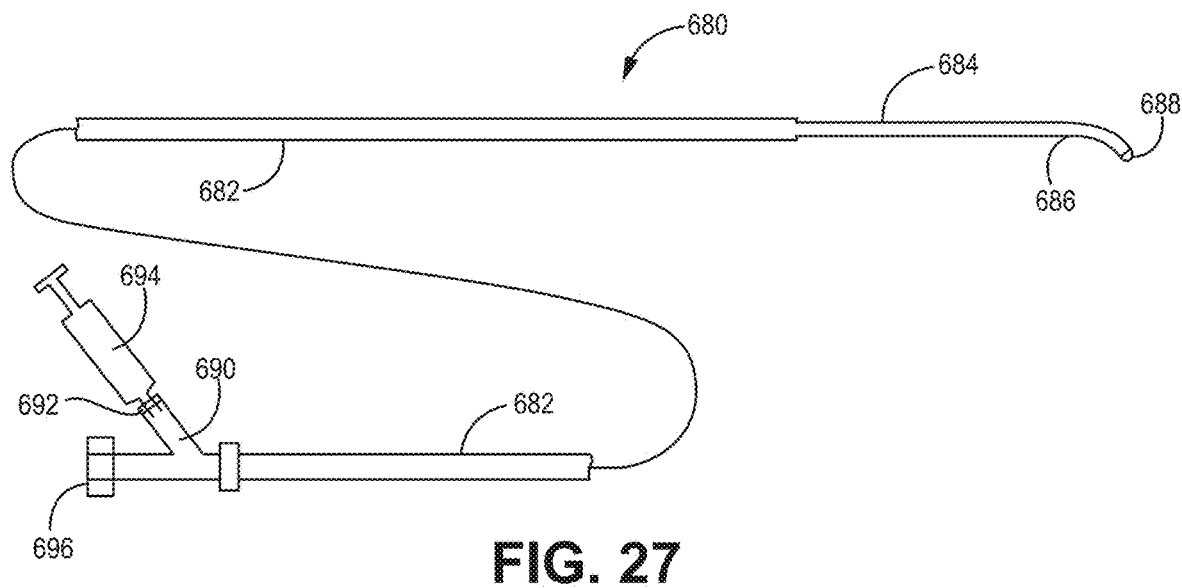
FIG. 27 is a side view of an aspiration catheter with a narrow distal tip.

Various aspiration catheters have been developed for providing improved suction within the narrow tortuous vessels of the cerebral vasculature. In some embodiments, these aspiration catheters have a narrowed distal tip that can reach into narrow vessels but provide high flows out of the vessel due to the larger proximal lumen. These improved designs are described in U.S. Pat. No. 9,662,129 to Galdonik et al., entitled "Aspiration Catheters for Thrombus Removal," incorporated herein by reference. Referring to FIG. 27, aspiration catheter 680 for accessing smaller vessels comprises a tube 682, a reduced diameter distal segment 684 with an average diameter smaller relative to the average diameter of the tube, an optional curved distal tip 686, a radiopaque marker band 688, which may be at or near the distal tip whether or not curved, a proximal end 690, an aspiration connection 692, a suction device 694, and a proximal port 696 for insertion of guide structures or other devices through the catheter lumen. Aspiration catheter 680 can optionally have a rapid exchange configuration with a rapid exchange port. Aspiration connection 692 can comprise a fitting or the like to provide a sealed connection with the suction device 694, or suction device 694 can be formed as an integral part of the proximal end 690 such that aspiration connection 692 is the integral connection. Suitable suction devices include, a suction device that can deliver a selected amount of suction, such as a syringe, a compressed bladder, a pump, such as a peristaltic pump or a piston pump, or the like.

Distal segment 684 can have an outer diameter from about 25 percent to about 95 percent of the average outer diameter of tube 682 of the catheter, and in further embodiments from about 45 to about 90 percent and in additional embodiments from about 60 to about 85 percent of the average diameter of the tube. For example, distal segment 684 can have an outer diameter range from about 0.015 to about 0.120 inches, and tube 682 can have an outer diameter range from about 0.030 to about 0.150 inches, in other embodiments from about 0.040 to about 0.125 inches and in further embodiments from about 0.045 to about 0.120 inches. A person of ordinary skill in the art will recognize that additional ranges of dimensions within the explicit ranges above are contemplated and are within the present disclosure. In optional embodiments, a bent or curved tip can provide improved tracking during delivery into a patient's vessel by controlling tracking along a guide structure extending from the tip.

Aspiration catheters with a narrowed distal segment approved and commercially available for neurovascular procedures include MI-AXIS™ (MIVI Neuroscience, Inc.) and MAX™ catheters (Penumbra). A new design is based on the use of a guide catheter to function as a part of aspiration lumen with a narrowed extension of the aspiration catheter extending from the guide catheter. See published U.S. patent application 2017/0143938 to Ogle et al., entitled "Catheter Systems for Applying Effective Suction in Remote Vessels and Thrombectomy Procedures Facilitated by Catheter Systems," incorporated herein by reference. An embodiment of these nozzle type aspiration catheters is shown in FIG. 28.

Figure 28:
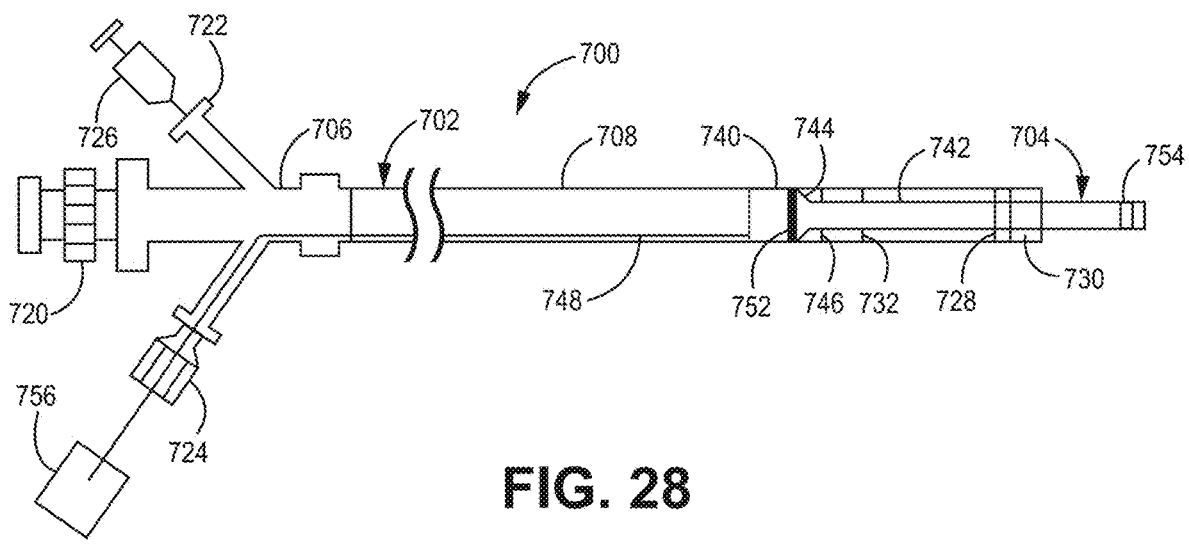
FIG. 28 is a side view of an aspiration system comprising a suction nozzle within a guide catheter and a corresponding proximal fitting with a flow manifold.

Referring to FIG. 28, suction system 700 comprises a suction adapted guide catheter 702 and a suction extension 704. The suction adapted guide catheter 702 comprises proximal section 706 and tubular shaft 708. Proximal section 706 generally is suitable for use also as a handle and generally can comprise a proximal fitting 720, a suction port 722 and an optional control wire port 724, as well as possibly other additional ports and/or fittings to provide desired functionality and access, in which all such ports and fittings can be arranged in a branch configuration or other suitable configuration. Proximal fitting 720 can comprise a suitable hemostatic valve, Luer fitting, Tuohy-Borst connector or the like to provide for entry of a guidewire and/or structures delivered over the guidewire into the guide catheter lumen, such as alternative treatment structures and/or embolic protection devices. As shown in FIG. 28, a negative pressure device 726 is shown connected with suction port 722, and suitable negative pressure devices include, for example, syringes, pumps, such as peristaltic pumps, piston pumps or other suitable pumps, aspirator/venturi, or the like.

Tubular shaft 708 can have an approximately constant diameter along its length, or the guide catheter can have sections with different diameters, generally with a smaller diameter section distal to a larger diameter section. Tubular shaft 708 can have one or more radiopaque marker bands to facilitate positioning of the tubular shaft within the patient, and FIG. 28 shows a marker band 728 near the distal end of tubular shaft 708, although additional positions and/or alternative positions can be used as desired. At or near the distal end of the shaft, a stop 730 is positioned to retain a portion of suction extension 704 within the lumen of tubular shaft 708. Tubular shaft 708 can further comprise a seal 732 to provide for reducing or eliminating any flow within tubular shaft 708 that avoids suction extension 704. In some embodiments, seal 732 can be combined with stop 730, or seal 732 as a distinct element can be avoided through a design with a sufficiently tight fit between suction extension 704 and the lumen wall of tubular shaft 708.

Suction extension 704 can comprises a proximal portion 740, suction tip 742, connection portion 744, optional engagement element 746 and control structure 748, such as a control wire. All or a part of proximal portion 740 can be configured to remain within the lumen of guide catheter 702. As shown in FIG. 28, proximal portion 740 comprises a radiopaque marker band 752, although proximal portion may not have a marker band in some embodiments and in other embodiments can comprise a plurality of marker bands. Suction tip 742 is shown with radiopaque marker band 754 near the distal tip of suction tip 742, although again suction tip 742 can comprise a plurality of radiopaque marker bands if desired. Connection portion 744 connects proximal portion 740 and suction tip 742, which can be a transition portion that gradually changes diameter or a connector that forms a seal between the proximal portion and suction tip. Optional engagement element 746 can engage stop 730 to establish the distal placement limit of suction extension 704 relative to guide catheter 702. In some embodiments, stop 730 is configured to engage an edge or other limiting structure of proximal portion 740 so that engagement element 746 is effectively integrated with the proximal portion 740 or connection portion 742. Control structure 748 can be a control wire or the like that connects with proximal portion 740 and extends exterior to the catheter, such as exiting through control wire port 724. Control structure 748 can be used to control positioning of proximal portion 740 within the lumen of tubular shaft 708. Control structure 748 can comprise a control tool 756, such as a handle, slide or other the like that can anchor a control wire or other connecting element to facilitate movement of the control wire. In some embodiments, the clearance can be made sufficiently small between the outer surface of proximal portion 740 and the inner surface of tubular shaft 708 that a separate seal is not needed.

The guide catheter can have an outer diameter from about 5.5 Fr (1.667 mm diameter) to about 10 Fr (3.333 mm diameter), in further embodiments from about 6 Fr (1.833 mm diameter) to about 9 Fr (3 mm diameter), and in some embodiments from about 6.25 Fr (2 mm diameter) to about 8.5 Fr (2.833 mm diameter). The guide catheter measurement are generally referenced to the outer diameter, and the inner diameter is less than the outer diameter by twice the wall thickness. The length of the guide catheter can be from about 30 cm to about 150 cm, in further embodiments from about 35 cm to about 130 cm and in additional embodiments from about 40 cm to about 120 cm. The length of suction extension 704 can be from about 30 cm to about 150 cm, in further embodiments from about 35 cm to about 130 cm and in additional embodiments from about 40 cm to about 120 cm. A person of ordinary skill in the art will recognize that additional ranges of dimensions within the explicit ranges above are contemplated and are within the present disclosure.

Guidewire, as used herein unless indicated otherwise, can refer to conventional guidewires or to guide structures that may have more structural features relative to a conventional guidewire. Guidewires for neurovascular applications are commercially available. These include TRANSEND® (Stryker) with a distal outer diameter (OD) of 0.014 inches (0.36 mm) and 0.0155 in (0.40 mm) proximal, SYNCHRO® (Stryker) with a range of diameters, CHIKAI™ (Asahi Intecc) with a 0.36 mm diameter and HEADLINER® (MicroVention/Turumo) with a range of diameters available. A guidewire for cerebral vessels with a hyperbolic corewire grind is described in published U.S. patent application 2016/0199620 to Pokorney et al. (hereinafter the '620 application), entitled "Medical Guidewires for Tortuous Vessels," incorporated herein by reference. These guidewires are suitable for appropriate procedures described herein.

Guide structure 658 over most of its length apart from any distal structure can have a diameter from about 0.005 inches to about 0.04, in further embodiments from about 0.007 inches to about 0.030 inches, in additional embodiments from about 0.0075 inches to about 0.020 inches and in other embodiments from about 0.008 inches to about 0.017 inches, with standard guidewire outer diameters being about 0.014 inches. The length of guide structure 658 can generally be selected for the particular procedure design. For example, for entry into the vasculature in the femoral artery for guiding into the cerebral arteries, guide structure 658 generally would have a length from about 190 cm (63 inches) to about 300 cm (106 inches), although shorter lengths such as 30 cm to 190 cm may be suitable for other entry vessels. A person of ordinary skill in the art will recognize that additional ranges within the explicit ranges for the diameters are contemplated and are within the present disclosure.

In general, guide structures 658 can be formed from one or more of various materials, such as polymers, metals and combinations thereof, although metals can provide convenient balance of strength, flexibility and deliverability to a target location in a cerebral vessel. Suitable materials are generally biocompatible in that they are non-toxic, non-carcinogenic and blood compatible and do not induce hemolysis or a significant immunological response. Suitable biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, and Nitinol®, a nickel-titanium alloy. Some of these metals are suitable for use as shape memory metals in which a particular shape is designed into the metal element upon formation, and the elements can be distorted to another shape for delivery and later allowed to resume its predesigned shape. Shape memory metals can be used for self-actuation, for example, with respect to fiber based filters referenced below. Suitable polymers for guide structures or portions thereof include, for example, polyether-amide block co-polymer (PEBAX®), nylon (polyamides), polyolefins, polytetrafluoroethylene, polyesters, polyurethanes, polycarbonates, polysiloxanes (silicones), polycarbonate urethanes (e.g., ChronoFlex AR®), mixtures thereof, or other suitable biocompatible polymers.

Guide structures generally can have a guidewire structure over most of its length but optionally can further include other features not directly related to the guidewire mechanical performance. For example, the '620 application describes a guide structure with a corewire that can be extended within the vessel to effectively increase the wire length available for device delivery. In some embodiments, a guide structure can comprise a filter or embolic protection device generally near its distal end. Fiber based filter devices have been found to be effective for delivery with a guide structure. Fiber based filter devices can comprise polymer fibers, which can be mixed with fibers of a biocompatible metal. Suitable polymers for the polymer fibers include, for example, polyamides (e.g., nylon), polyesters (e.g., polyethylene terephthalate), polyacetals/polyketals, polyimide, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones (PEEK), ethylene vinyl acetates, polysulfones, nitrocelluloses, similar copolymers and mixtures thereof.

Embolic protection devices with small filter lateral extent and designed for suitable manipulations to facilitate delivery in vessels have been developed that are suitable for use in the medical systems described herein. See, for example, U.S. Pat. No. 7,879,062B2 to Galdonik et al., entitled "Fiber Based Embolic Protection Device," and U.S. Pat. No. 8,092,483B2 to Galdonik et al., entitled "Steerable Device Having a Corewire Within a Tube and Combination with a Medical Device," both of which are incorporated herein by reference. FiberNet® embolic protection devices based on the technology in these patents are commercially available from Medtronic Inc. These fiber based embolic protection devices comprise a guide structure with a corewire that allows for deployment of the embolic protection device using an actuator at the proximal end outside of the patient.

Additional fiber-based filter devices particularly designed for delivery into tortuous vessels, such as cerebral arteries, are described in U.S. Pat. No. 8,814,892B2 to Galdonik et al. (hereinafter the '892 patent), entitled "Embolectomy Devices and Method of Treatment of Acute Ischemic Stroke Condition," incorporated herein by reference. The fiber based filters generally comprise polymer fibers that provide a low abrasion surface against the vessel wall but may also include some metal fibers/wires to add mechanical strength to the filter, which can be incorporated into the structure to avoid abrasion to the vessel wall. The '892 patent describes the use of the filter device as a clot engagement tool for use with an aspiration catheter. The '892 patent also envisions the use of supplementary structures to facilitate engagement of the clot. Further embodiments of fiber based filter devices are described in the '061 application. These filters can be deployed using a microcatheter or other structure.

As described further below, procedures can use guidewires to facilitate access to desired locations in the vessel, and may be removed at some point during the process. As described above, a balloon/inflation catheter may be unassociated with a wire, may have an integral fixed wire, or may have a design to allow for riding over a guidewire. The catheter designs allowing for delivery over a guidewire (see FIGS. 8, 16 (some embodiments), 18 and 22) may be used with guide structures that have embolic protection structures at their distal end.

The use of additional treatment structure 660 or a plurality thereof are also contemplated as an option in procedures described herein. Suitable devices as additional treatment structure 660, for example, can apply mechanical forces to a clot to facilitate removal of the clot. With respect to additional treatment structure 660, suitable devices include, for example, angioplasty balloons, stent delivery devices, atherectomy devices, such as stent retrievers, and the like. Stents may be, for example, balloon extendable, self-extendable or extendable using any other reasonable mechanism. Balloon extendable stents can be crimped to the balloon for delivery. Some balloon-stent structures are described further, for example, in U.S. Pat. No. 6,106,530, entitled "Stent Delivery Device;" U.S. Pat. No. 6,364,894, entitled "Method of Making an Angioplasty Balloon Catheter;" and U.S. Pat. No. 6,156,005, entitled "Ballon [sic] Catheter For Stent Implantation," each of which are incorporated herein by reference. Self-expanding stents are described further in U.S. Pat. No. 8,764,813 to Jantzen et al., entitled "Gradually Self-Expanding Stent" and U.S. Pat. No. 8,419,786 to Cottone, Jr. et al., entitled "Self-Expanding Stent," both of which are incorporated herein by reference. Stent retrievers are described, for example, in U.S. Pat. No. 8,795,305 to Martin et al., entitled "Retrieval systems and methods of use thereof," incorporated herein by reference. Stent retrievers with a flexible frame and a polymer cover to provide a gentler interface with a vessel wall are described in detail in the '061 application. A stent retriever as described in the '061 application can be used and removed prior to the delivery of a balloon/infusion catheter.

As described above, a microcatheter can be used as a component of a balloon/infusion system (see FIG. 1), and microcatheters may be used for other purposes during a procedure. Microcatheters have been designed to allow for access to small blood vessels, such as cerebral blood vessels, and cerebral microcatheters are available commercially, e.g. Prowler Select™ (Cordis Neurovascular Inc.) and Spinnaker Elite™ (Boston Scientific Co.). Of course the term microcatheter can cover a range of devices, and the present discussion can focus on catheters useful for the procedures described herein. In some embodiments, microcatheters can comprise a distal section that is narrower than a proximal section. However, in further embodiments, a microcatheter can have an approximately constant diameter along its length to facilitate delivery of other devices over the microcatheter. A narrow distal diameter allows for the catheter to navigate the tortuous vessels of the brain. The distal section can be highly flexible enough to navigate the vessels, but resilient enough to resist kinking. A microcatheter comprises at least one lumen. The microcatheter can then be used to deliver (or provide) other treatment devices, aspiration flow, therapeutic agents, or the like, or combinations thereof. While microcatheters can have a selected size, in some embodiments, the microcatheters can have a distal outer diameter from about 1.0 Fr to about 3.5 Fr and in further embodiments from about 1.5 Fr to about 3 Fr, and a length from about 30 cm to about 200 cm and in further embodiments from about 45 cm to about 150 cm. A person of ordinary skill in the art will recognize that additional size ranges within the explicit ranges above are contemplated and are within the present disclosure.

Backend fitting 662 can comprise suitable structures, which may be unitary with a catheter or in separate components with appropriate connectors, for assembly and operation of treatment system 650. For example, various conventional connectors can be associated with the fitting to facilitate connections of the devices, and suitable connectors include, for example, tuohy-borst connectors, Luer connectors, or the like. As noted above, a guide catheter generally comprises a hemostatic valve, but backend fitting 662 can comprise one or more additional hemostatic valves if suitable for the use of the various components as a system. A hemostatic valves allows for passage of devices into a catheter with little or no blood loss and are commercially available. Backend fitting 662 can comprise a manifold structure with optional branches to provide desired connectors or attachment of additional fittings. For example, backend fitting 662 can comprise one or multiple Y-branches or alternative branching structures that can provide, for example, connectors for infusion fluid source 664, balloon inflation fluid source 666, aspiration source 668, or combinations thereof.

Infusion fluid source 664 and balloon inflation fluid source 666 can be distinct structures or can be combined as a single structure if a lumen balloon/inflation catheter uses a common lumen for both balloon inflation and infusion. Suitable structures for infusion fluid source 664 and balloon inflation fluid source 666 can comprise a reservoir of fluid and fluid delivery structure. Fluid delivery structures can be manual or mechanical, such as a syringe, a compressed bladder, pump, such as a peristaltic pump or a piston pump, or the like. Balloon inflation fluid source 666 (or a combined fluid source) generally is also reversible to remove fluid when desired to deflate a balloon.

A reservoir of infusion fluid generally comprises a biocompatible liquid, such as sterile buffered saline, compatible blood, such as the patient's own blood or appropriately typed blood, or the like in a selected volume for the procedure, although a balloon inflation fluid source, in principle, can comprise a wider range of fluids if not used for infusion and maintained to not enter the patient. An infusion liquid can further comprise a drug, such as a clot dissolving drug, an antispasm drug or combinations thereof. Since the liquid is aspirated from the vessel, generally relatively large amounts of drug can be delivered for short time availability in the treatment region. Suitable clot dissolving drugs include, for example, tPA (tissue Plasminogen Activator). The infusion reservoir can comprise a volume from about 0.1 cc (cubic centimeters) to about 50 cc, in further embodiments from about 0.2 cc to about 35 cc, and in additional embodiments from about 0.25 cc to about 25 cc. A person of ordinary skill in the art will recognize that additional ranges of volumes within the explicit ranges above are contemplated and are within the present disclosure. Aspiration source 668 can be any suitable negative pressure device. Suitable negative pressure devices include, for example, syringes, pumps, such as peristaltic pumps, piston pumps or other suitable pumps, aspirator/venturi, or the like. Suitable pumps are available from Allied Healthcare Products, Inc., and are distributed by Mivi Neuroscience, Inc.

Procedure

The procedures described herein are generally designed to provide clot removal based on aspiration and infusion. The resulting hydraulic and hydrodynamic forces from a resulting flow can provide for an effective process for clot removal with an objective of less trauma on the vessel wall and surrounding tissue. The overall procedure provides for accessing the vessel, e.g., a cerebral vessel, past a clot. A balloon/infusion catheter is placed with the balloon and infusion port(s) located distal to the clot, and an aspiration catheter is place with an aspiration port proximal to the clot. Flow is then established with infusion and aspiration simultaneously applied, although not necessarily through the entire time of applying each flow. The resulting fluid flow facilitates moving the clot or portions thereof to the aspiration catheter and/or into the aspiration catheter. The following discussion focuses on a procedure to remove a clot in a cerebral artery inducing an acute ischemic stroke event, and a person of ordinary skill in the art can adapt this discussion for other arteries or other vessels within a patient based on the discussion herein.

Figure 29:
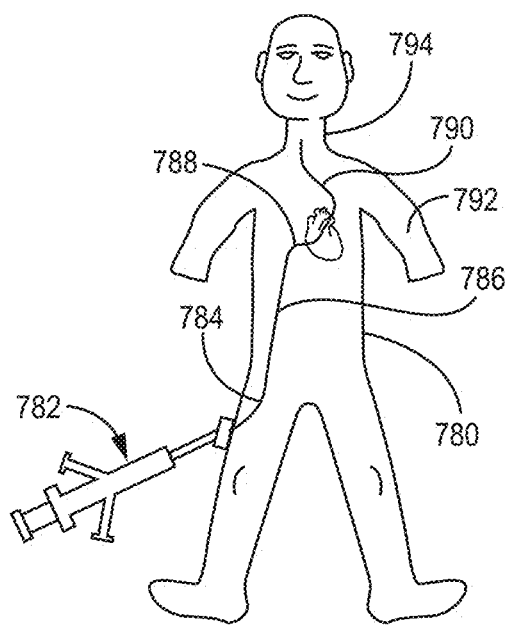
FIG. 29 is a schematic diagram of a patient depicting delivery of a stroke treatment system percutaneously with entry into a femoral artery.

Referring to FIG. 29, a human patient 780 is shown with appropriate portions of a treatment system 782 inserted into their femoral artery 784 where components are guided up the descending aorta 786 around the aortic arch to the ascending aorta 788 where components are guided into a carotid artery 790 (left or right) prior to reaching the heart. The distal end of the components are then guided through the patient's neck into an internal carotid artery and then into the cerebral arteries forming the neurovasculature. While this can be a desirable approach to the cerebral arteries, alternative access locations include the arm 792 or the neck 794. Radiopaque markers generally are used to assist with placement of the various devices including placement of the balloon and infusion port(s) distal to the clot using real time imaging.

Figure 30:
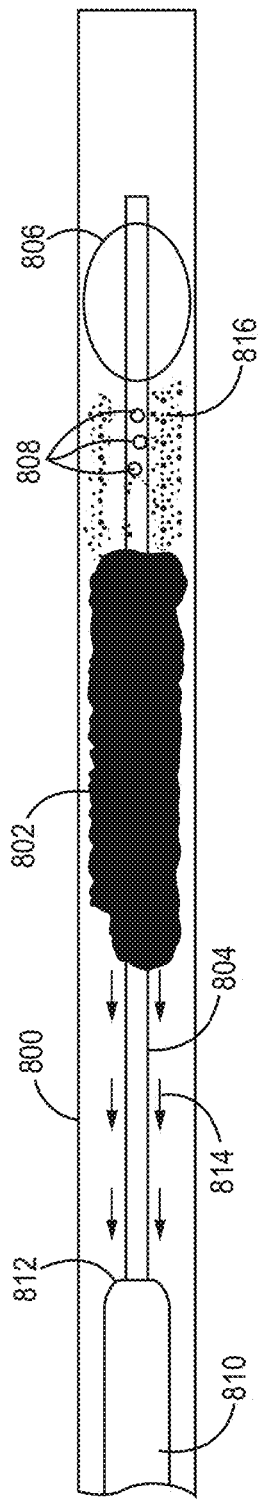
FIG. 30 is a fragmentary view of a balloon/infusion catheter deployed in a patient's vessel and an aspiration catheter positioned to establish hydraulic forced to push a clot in a distal to proximal direction toward the aspiration catheter.

The basic arrangement for the performance of the procedure is shown schematically in FIG. 30. As noted above, the basic concept is to generate hydraulic forces between an expanded occlusion balloon and the aspiration catheter to dislodge the clot. As shown in FIG. 8, a treatment system is positioned within a patient's vessel 800, e.g., an artery. Clot 802 is lodged within vessel 800. Balloon/infusion catheter 804 is positioned within vessel 800 with balloon 806 inflated distal to clot 802 and with infusion ports 808 positioned between clot 802 and balloon 806. Aspiration catheter 810 is positioned over balloon/infusion catheter 804 with the aspiration opening 812 within vessel 800 proximal to clot 802. Flow arrows 814 indicate flow resulting from aspiration, and infusion fluid 816 injected into vessel 800 between balloon 806 and clot 802 is shown with shading. Hydraulic forces on clot 802 in a distal to proximal direction are generated by infusion fluid 816 distal to the clot and suction applied by the aspiration catheter proximal to clot 802.

Preliminary preparations for the percutaneous procedure can comprise access into the arterial system along with placement of hemostatic fittings and other appropriate components providing access into the patient. In some embodiments, access is obtained into a femoral artery, although other access locations can be used. For access through the femoral artery, the devices can comprise guides up the aorta to entrances to the common carotid artery from which access into the cerebral vasculature can be obtained. In some embodiments, a guide catheter is placed with its distal end in a carotid artery, such as an internal carotid artery, to facilitate subsequent steps of the procedure. The guide catheter can have a balloon, and whether or not the guide catheter has an occlusion balloon, the guide catheter may or may not be used for suction.

Common features of the procedures described herein comprise obtaining access to the cerebral artery distal to a clot, which is generally performed with a guide structure, e.g., a guidewire. A position distal to the clot is generally maintained until the clot is removed at least in part. Once a guide structure has established position, the components can be delivered over the guide structure. At some point, a balloon/infusion catheter is delivered to position the balloon distal to the clot and infusion port(s) between the balloon and the clot. A microcatheter may or may not be involved in the delivery process, and the guidewire may or may not be removed prior to the placement of the balloon/infusion catheter. To maintain position distal to the clot, a microcatheter generally is used if the guidewire is removed prior to the placement of the balloon/infusion catheter. Also, an aspiration catheter is placed prior to initiation of hydraulic forces, although a guide catheter can be used for aspiration. If a balloon/infusion catheter can ride over a guide structure, a wire based treatment device can be delivered through a microcatheter prior to delivery of the balloon/infusion catheter. Using fluid flow, the clot or portions thereof are removed from the vessel. The components of the treatment system can be removed using a reasonable procedure designed to avoid release of emboli. While this order of steps accounts for practical implementation and provides an overview of the procedure, reasonable variation in the order of steps can be used if consistent with the overall procedure. Thus, appropriate steps may be performed in a different order, and some steps can be performed in substeps that may be interspersed with portions of other steps. Also, repositioning of various components can take place through the procedure as appropriate and desired by the user.

Figure 31:
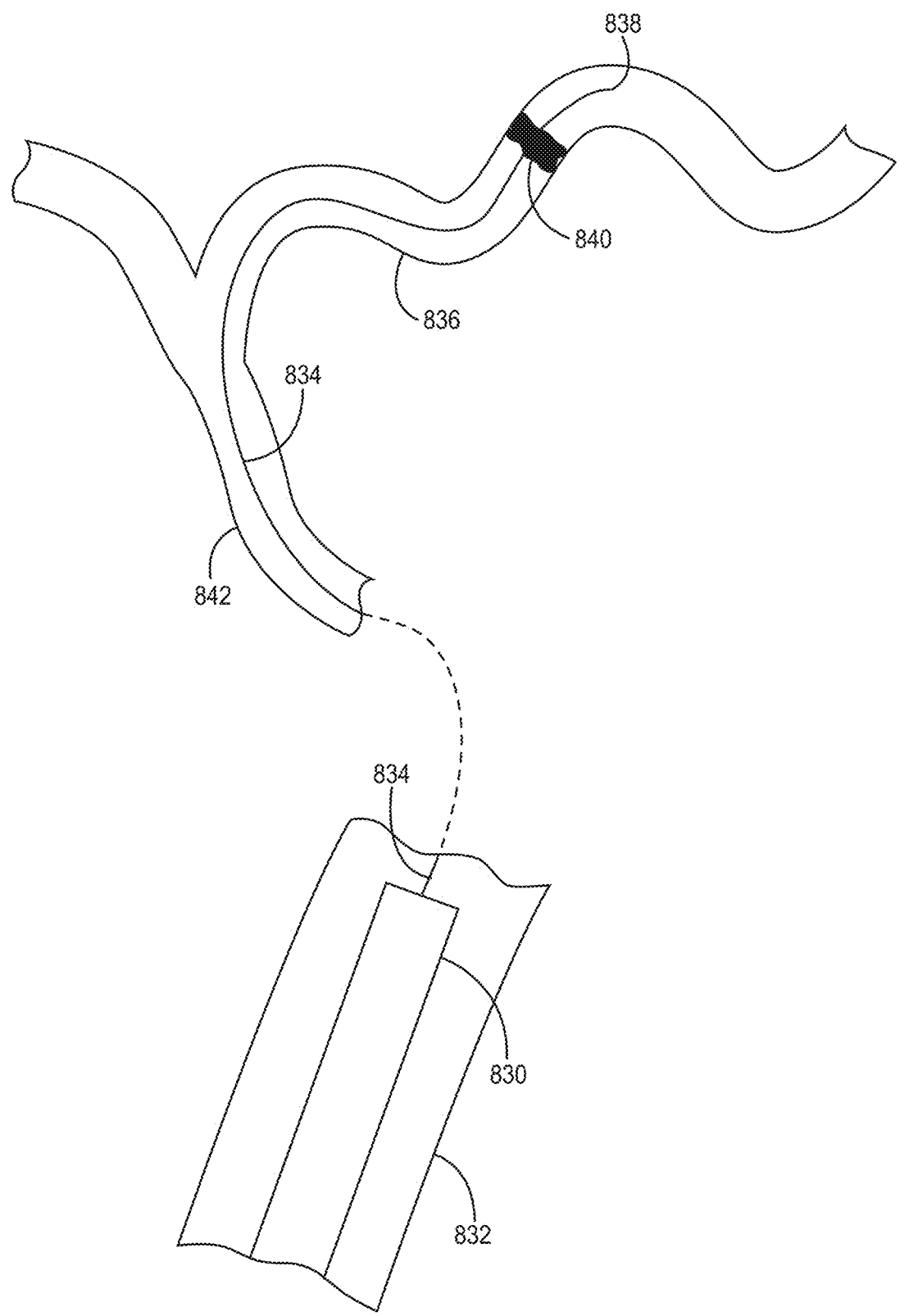
FIG. 31 is a fragmentary view of a portion of carotid artery with a distal end of a guide catheter positioned in the carotid artery and with a guidewire extending out from the guide catheter into a cerebral artery with the distal end of the guidewire extending past a clot.

In some embodiments, to perform the procedure, generally a guidewire is positioned with its distal end extending beyond the clot following insertion through or past the clot. FIG. 31 depicts a neurovascular artery with a clot and a guidewire positioned in the artery. The guidewire can then be used to guide delivery of the additional components for the procedure. Referring to FIG. 31, a guide catheter 830 can be placed in the carotid artery 832. A guidewire 834 is guided past carotid artery 832 into a cerebral artery 836 with its distal tip 838 positioned past a clot 840. A vascular path truncated in the figure from carotid artery 832 to an upstream cerebral artery 842 branching into cerebral artery 836 is depicted with a dashed line to note portions of the path not depicted for simplicity of drawing. This step is generally significant with respect to accessing the desired location distal to the clot, and this position distal to the clot is generally maintained until the thrombus from the clot is moved to a more proximal location or removed from the patient.

Figure 32:
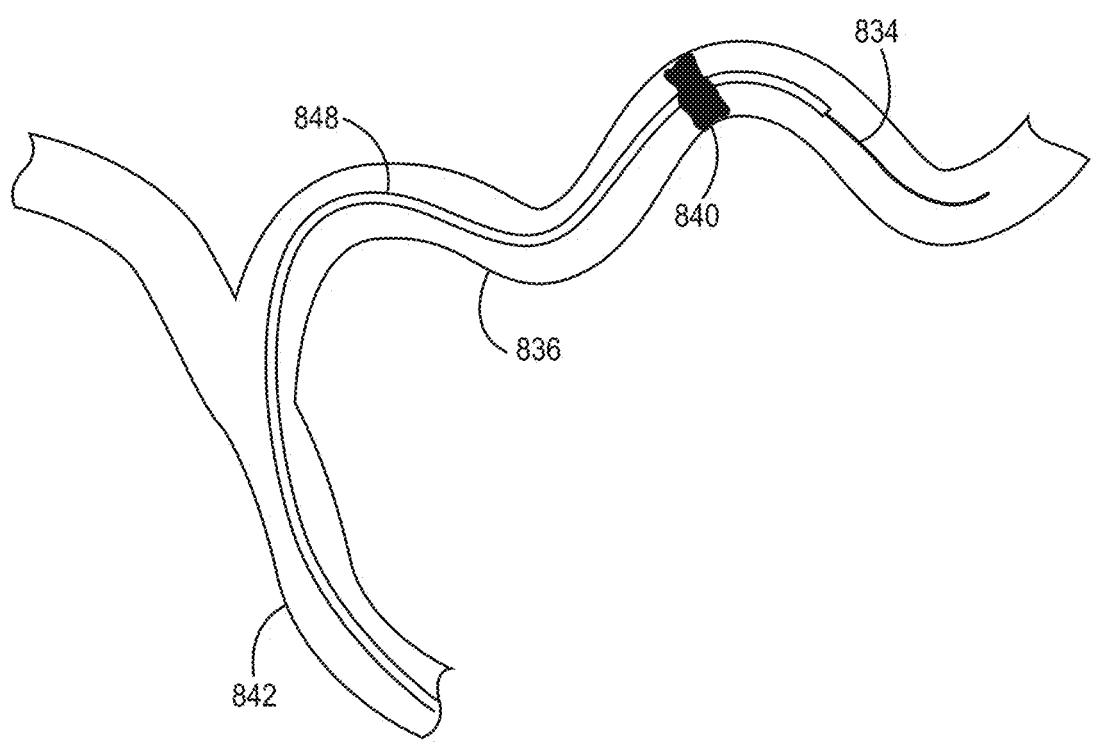
FIG. 32 is a fragmentary view of the cerebral artery of FIG. 31 with a microcatheter delivered over the guidewire such that the distal end of the microcatheter extends past the clot.

The next steps can depend on whether or not the balloon/infusion catheter can ride over a guide structure. The next FIGS. are focused on embodiments of a balloon/infusion catheter (with one or more lumen) that are not designed to ride over a guide structure whether or not they have a fixed wire, although a balloon/infusion catheter capable of delivery over a guide structure can be used without riding over guide structure assuming an adequate seal can block flow into a catheter lumen when a guide structure is not present. Following this discussion, potential alterations of the procedure are discussed if the balloon/infusion catheter rides over a guide structure during the procedure. Referring to FIG. 32, a microcatheter 848 is positioned over guidewire 834 with its distal tip past clot 840. Once microcatheter 848 is in position, guidewire 834 can be removed while maintaining access distal to the clot using the microcatheter.

Figure 33:
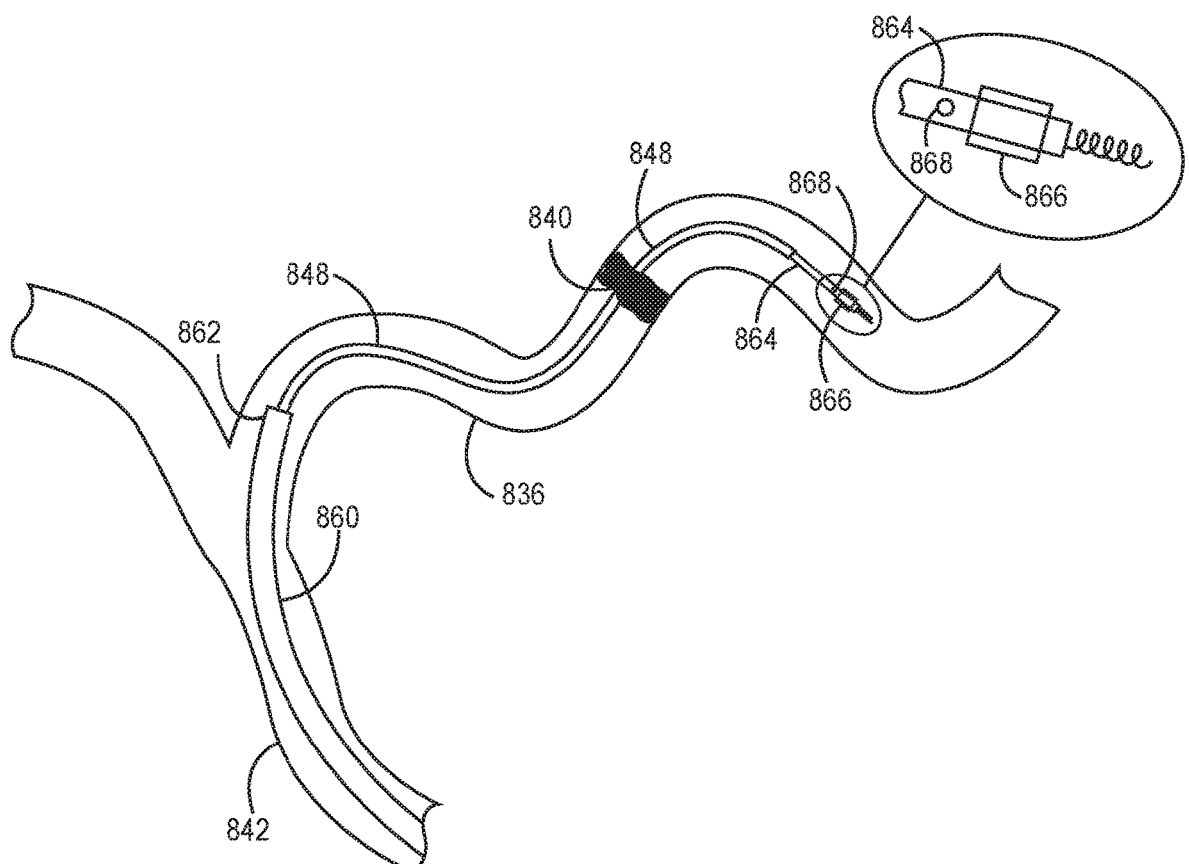
FIG. 33 is a fragmentary view depicting the cerebral artery of FIG. 32 with an aspiration catheter put in place and the guidewire removed and replaced with a balloon/infusion catheter in which the balloon is not inflated.

Either before or after guidewire 834 is removed, aspiration catheter 860 can be positioned with its distal tip 862 entering cerebral vessel 836, as shown in FIG. 33. Depending on the specifics of the vasculature and the aspiration catheter design, aspiration catheter distal tip may be brought closer or further from clot 840, and the aspiration catheter can be in an upstream cerebral artery 842 at an appropriate position. It can be understood from the discussion above, that in the context of the procedure, reference to an aspiration catheter can similar involve an aspiration nozzle that is part of an aspiration system, and such alternative use of aspiration components is intended for all of the embodiments in this section on the procedure. A medical professional performing the procedure can adjust the procedure accordingly based on the position of the aspiration catheter.

Figure 34:
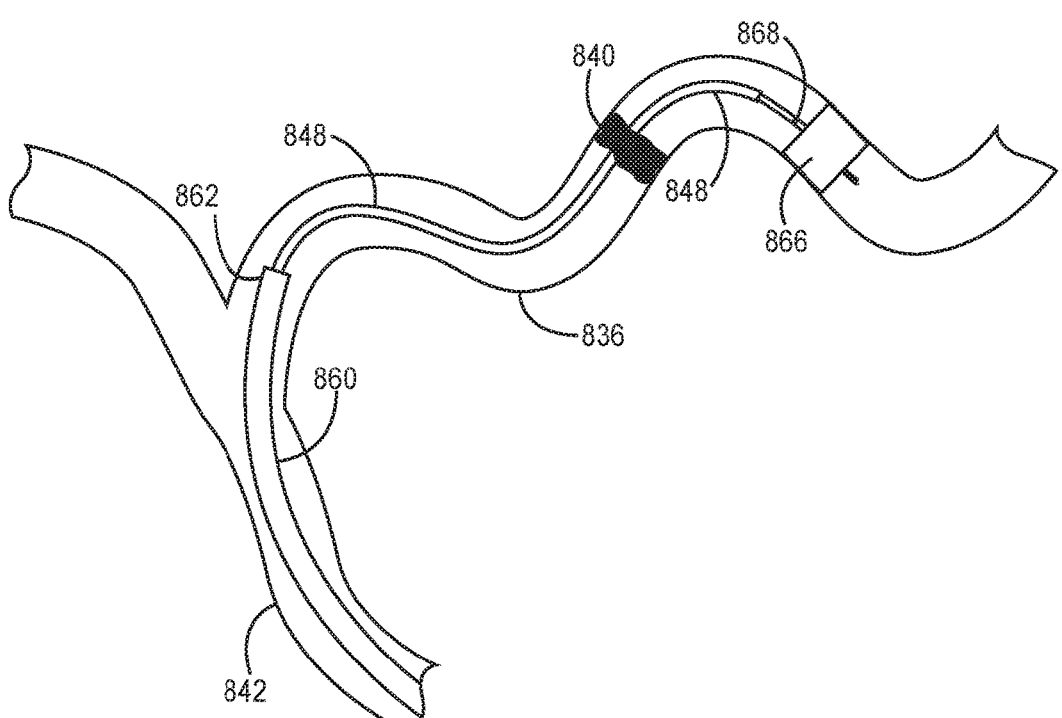
FIG. 34 is a fragmentary view depicting the cerebral artery of FIG. 33 in which the balloon of the balloon/infusion catheter is inflated.

Referring to FIG. 33, following removal of guidewire 834, a balloon/infusion catheter 864 is delivered through microcatheter 848 to place balloon 866 and infusion port(s) 868 past clot 840. The order of delivery of aspiration catheter 860 and balloon/infusion catheter 864 generally can be selected as desired. Referring to FIG. 34, balloon 866 is inflated to inhibit flow in either direction past the balloon.

Aspiration and infusion generally are initiated following inflation of balloon 866. Also, aspiration and infusion can be initiated approximately simultaneously or sequentially with a planned time spacing, and even if planned to be approximately simultaneous, the processes are generally separately initiated so that a slight delay generally results from the time to start the processes. In practice, a medical professional may develop a technique according to personal preferences with respect to the order of inflating the balloon, starting aspiration, and starting infusion. For example, a professional may want to start aspiration, and then inflate the balloon followed by infusing liquid. Generally, any reasonable process order can be used with appropriate attention to avoiding the flow of emboli downstream in the vessel based on release of thrombus from the clot.

Figure 35:
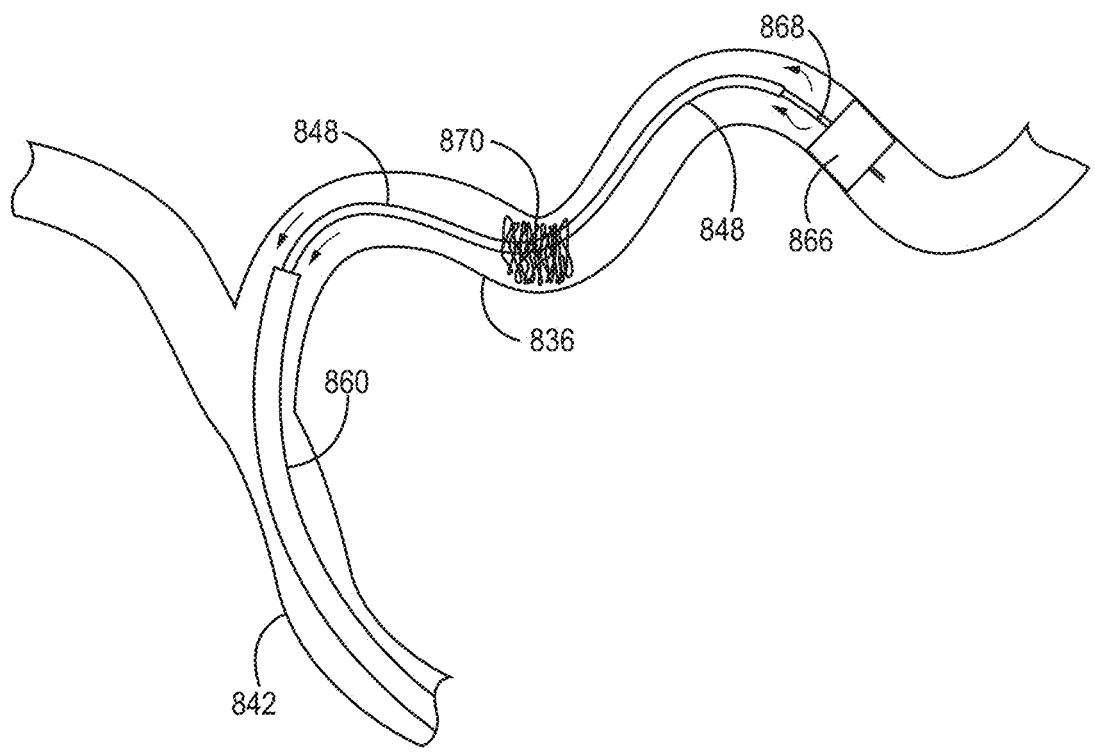
FIG. 35 is a fragmentary view depicting the cerebral artery of FIG. 34 in which hydraulic forces are established with aspiration and infusion resulting in the movement of thrombus from the clot in a proximal direction.

Referring to FIG. 35, aspiration is depicted with flow arrows near the aspiration opening into aspiration catheter 860 and flow arrows near infusion port 868 indicate infusion into the vessel of infusion liquid. Due to the occlusion effect of the clot, the infusion of liquid initially tends to increase the pressure between the clot and the balloon. A pressure increase tends to increase the vessel diameter in response if the vessel wall has some elasticity. The infusion pressure and liquid volume can be controlled to avoid damage to the vessel. The amount of liquid delivery by infusion may optionally change as the clot is dislodged and liquid can flow more readily to the aspiration catheter. Regardless, the hydraulic pressure established by the aspiration from the proximal position and infusion from a distal position established hydraulic forces moving in a distal to proximal direction.

Figure 36:
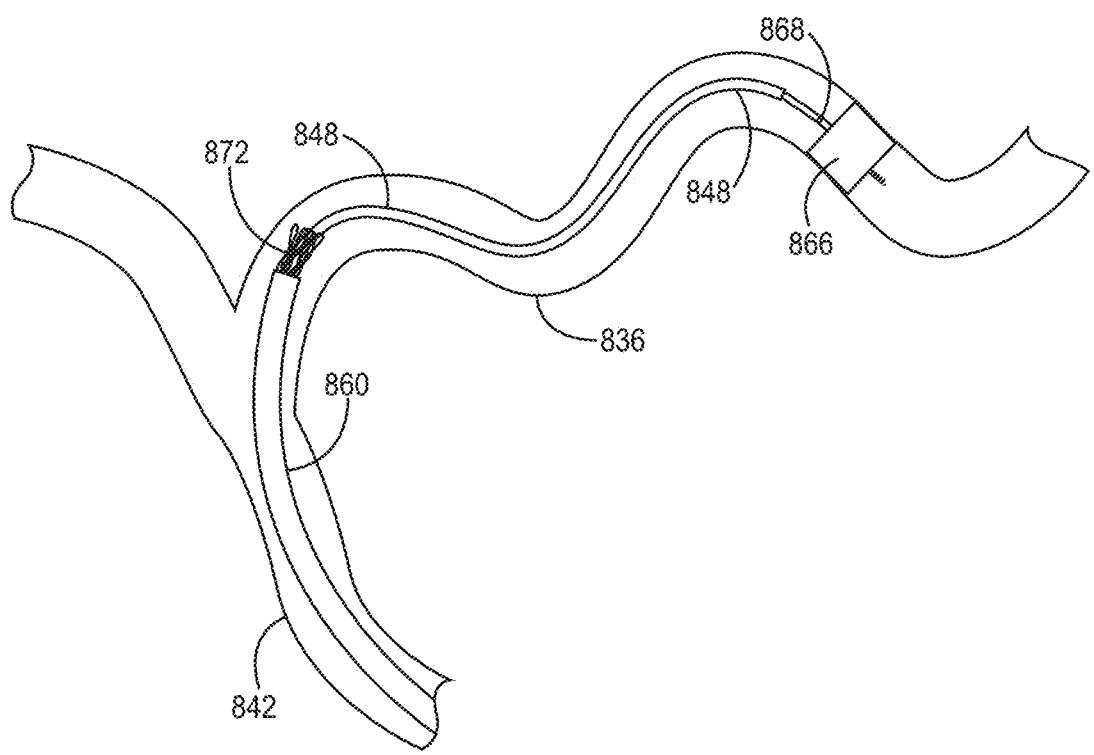
FIG. 36 is a fragmentary view depicting the cerebral artery of FIG. 35 in which thrombus from the clot has reached the aspiration opening of the aspiration catheter.

Referring to FIG. 35, due to the hydraulic forces in cerebral vessel 836, thrombus 870 from clot 840 moves in a proximal direction. Continued movement of thrombus results in captured thrombus removed by aspiration catheter 860 and/or captured thrombus 872 at the opening into aspiration catheter 860, as shown in FIG. 36. Depending on the size of the clot and rigidity of the clot material, the clot may or may not completely enter into the lumen of the aspiration catheter. Thrombus may fragment during the removal process with a portion of thrombus from clot 840 removed through aspiration catheter 860 and a portion of thrombus captured at the opening of aspiration catheter 860 or generally any amounts on the continuum of all of the thrombus removed by aspiration or all of the thrombus collected on the tip of aspiration catheter 860. Infusion flow can be reduced or turned off if aspiration flow diminishes due to occlusion or partial occlusion of the aspiration catheter by the clot.

Figure 37:
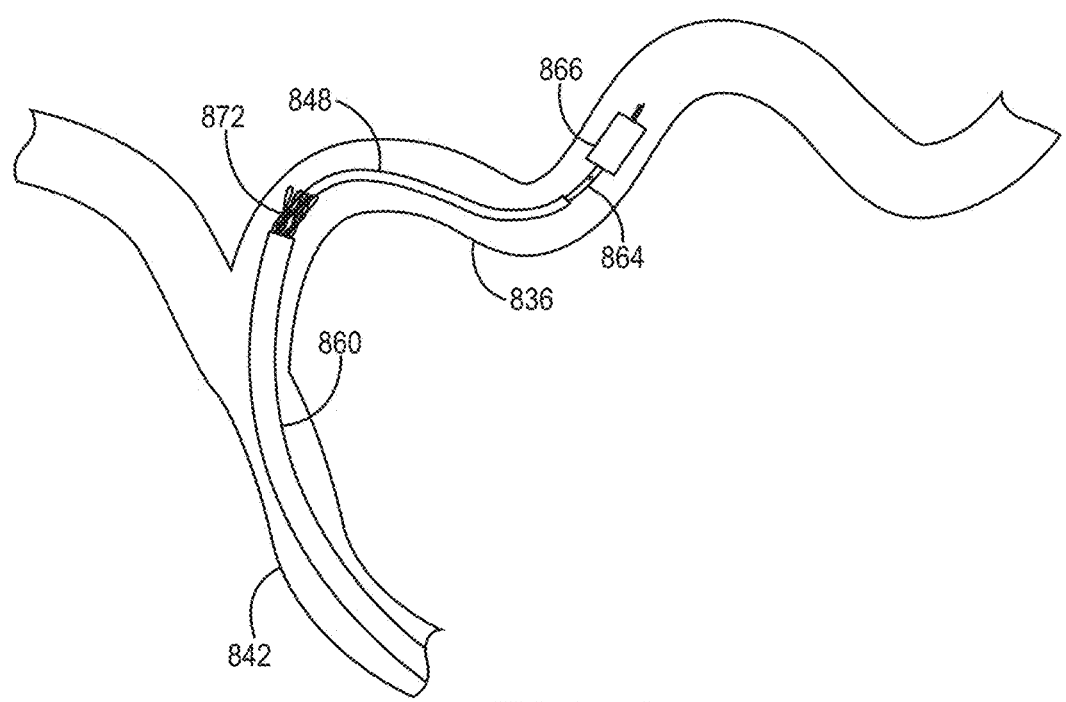
FIG. 37 is a fragmentary view depicting the cerebral artery of FIG. 36 in which the balloon is at least partially deflated and the microcatheter and balloon/infusion catheter are being removed from the vessel.

Following appropriate capture of thrombus, balloon 866 can be deflated, partially or approximately fully deflated, and then removed from the vessel. Referring to FIG. 37, balloon 866 is partially deflated, and removal from cerebral artery 836 has been initiated. Microcatheter 848 can be removed simultaneously with balloon/infusion catheter 864 or separately, prior to or after if balloon is essentially fully deflated. In some embodiment, microcatheter 848 can be removed at least partially into a more proximal position following delivery of balloon/infusion catheter 864 prior to removing clot 840 to provide a slightly increased volume of an aspiration lumen between the inner wall of aspiration catheter 860 and devices passing within aspiration catheter 860. As shown in FIG. 37, microcatheter 848 is removed simultaneously with balloon/inflation catheter 864.

Aspiration may or may not be maintained during the device removal process or separate portions thereof at the same pressure or a reduced pressure or combination thereof at different times. Infusion is generally stopped prior to deflating balloon 866. Aspiration catheter 860 can be removed simultaneously with balloon/infusion catheter 864 or following removal of balloon/infusion catheter 864. In some embodiment, aspiration catheter 860 is maintained in position until balloon 866 is withdrawn close to the opening into aspiration catheter 860 following which catheters 860, 864 are removed together. In general, a selected order for removing aspiration catheter 860 and balloon/infusion catheter 864 can be selected in various reasonable orders and variants thereof with some consideration that medical professionals may develop preferences based on their experiences and further clinical studies may suggest specific nuances of the procedures. The order of removal of the components can be selected to facilitate removal of the thrombus with a low risk of embolization from the thrombus. Ultimately, all of the devices of the system are removed from the patient and entry point into the patient is closed.

Figure 38:
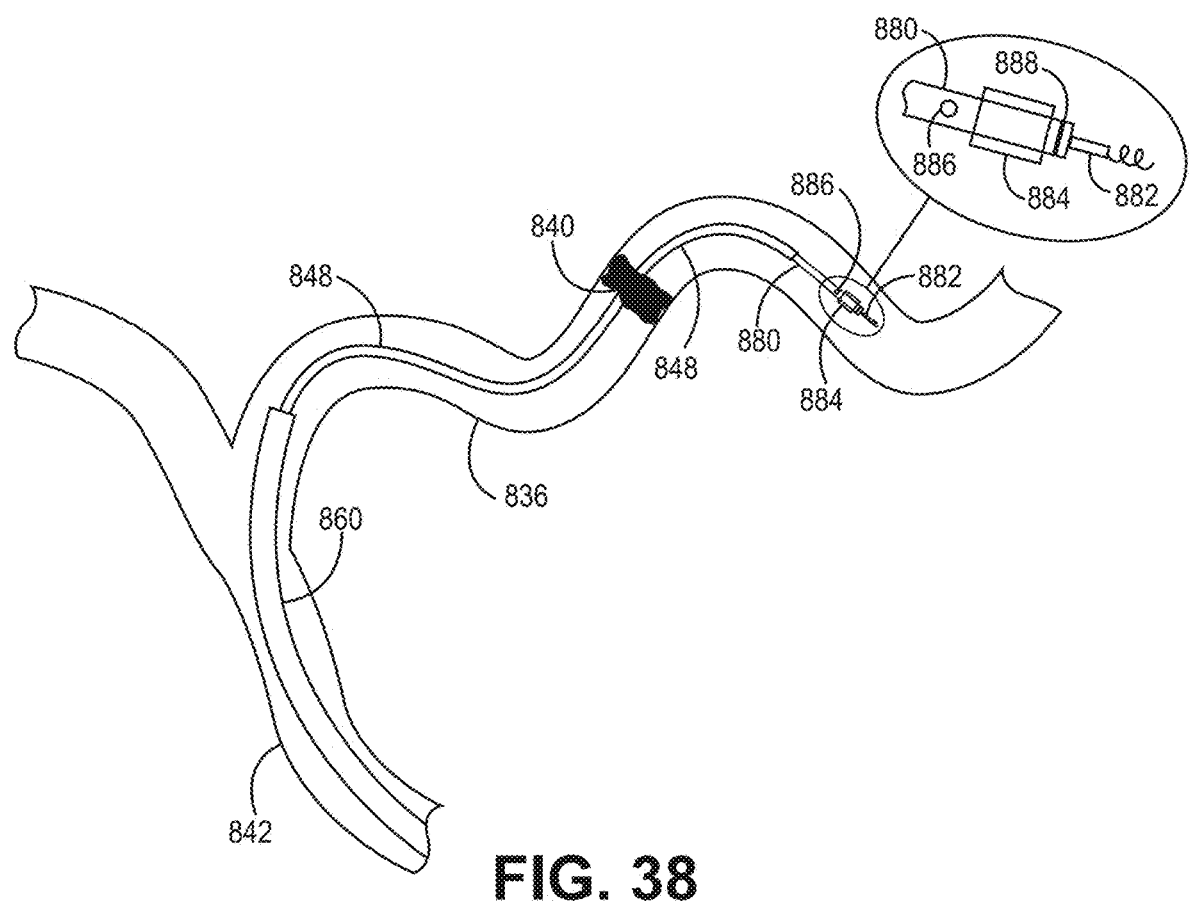
FIG. 38 is a fragmentary view depicting an alternative portion of the procedure in which a balloon/infusion catheter is delivered over the guidewire as an alternative to the steps leading to the configuration shown in FIG. 34.

If the balloon/infusion catheter can ride over a guidewire, various additional options for the procedure are available. For such embodiments, a microcatheter may not be used since the microcatheter is not needed to maintain access to a location distal to the clot. Nevertheless, an option is to still use a microcatheter to facilitate delivery of the balloon/infusion catheter. Such an embodiment is shown in FIG. 38, although an embodiment without the use of a microcatheter would look similar with just microcatheter 848 absent. Referring to FIG. 38, the vessel, clot and ancillary devices are shown to be the same as in FIGS. 32 to 37, but with a balloon/infusion catheter 880 riding over guide structure 882. Referring to FIG. 38 and the insert blow up, balloon/infusion catheter 880 comprises balloon 884, infusion port(s) 886 and valve/seal 888. Assuming that valve/seal 888 can provide an appropriate closure, guide structure 882 can be removed in some embodiments following placement of balloon/infusion catheter 880. Once balloon/inflation catheter 880 is in position, the procedure can continue as described in the context of FIGS. 34-37, except for appropriate consideration of the removal of guide structure 882 and suitable adjustments if no microcatheter is used. Guide structure 882 can be removed simultaneously with balloon/infusion catheter 880 or earlier in the procedure if leakage of blood into balloon/infusion catheter 880 does not occur significantly or is not a concern at the particular stage of the procedure, such as after deflating balloon 884.

Additional embodiments of the procedure can be considered when a balloon/inflation catheter can ride over a separate guide structure. Specifically, an initial guidewire can be replaced by alternative treatment structures, such as a filter mounted on a guide structure. In these embodiments, a microcatheter is used to maintain access to a position distal to a clot at least until placement of a treatment device to maintain a position distal to the clot. The steps in the procedure in FIGS. 31 and 32 can be the same. With microcatheter 848 in place as shown in FIG. 32, guidewire 834 can be removed and replaced with a device 900, which can be a guide structure with a filter or alternative treatment structure. For illustrative purposes, structure 900 is described and shown in the context of FIG. 39 as a guide structure with a filter 902 near its distal end. As noted above, filter 902 can be deployed with a proximal actuator using a corewire, self-actuation upon release from the microcatheter, deployment using the microcatheter or alternative structure as an actuation tool, or a combination thereof. In some embodiments, filter 902 is deployed prior to delivery of a balloon/infusion catheter, although depending on the actuation mechanism, filter 902 may be deployed following delivery of a balloon/infusion catheter or using balloon/infusion catheter itself as an actuation tool for the filter.

Figure 40:
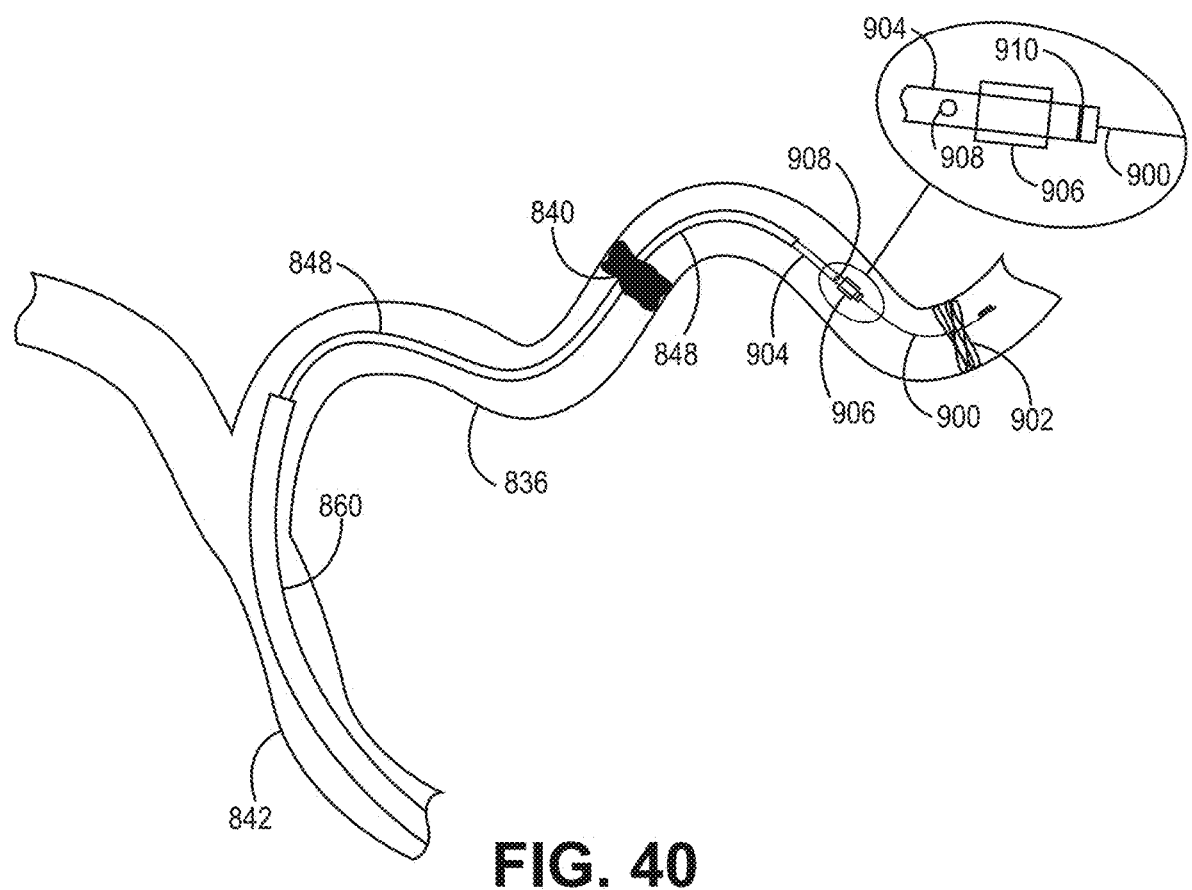
FIG. 40 is a fragmentary view of the cerebral artery of FIG. 39 in which the fiber based filter is deployed and a balloon/infusion catheter is put into position riding over the guide structure.
Figure 39:
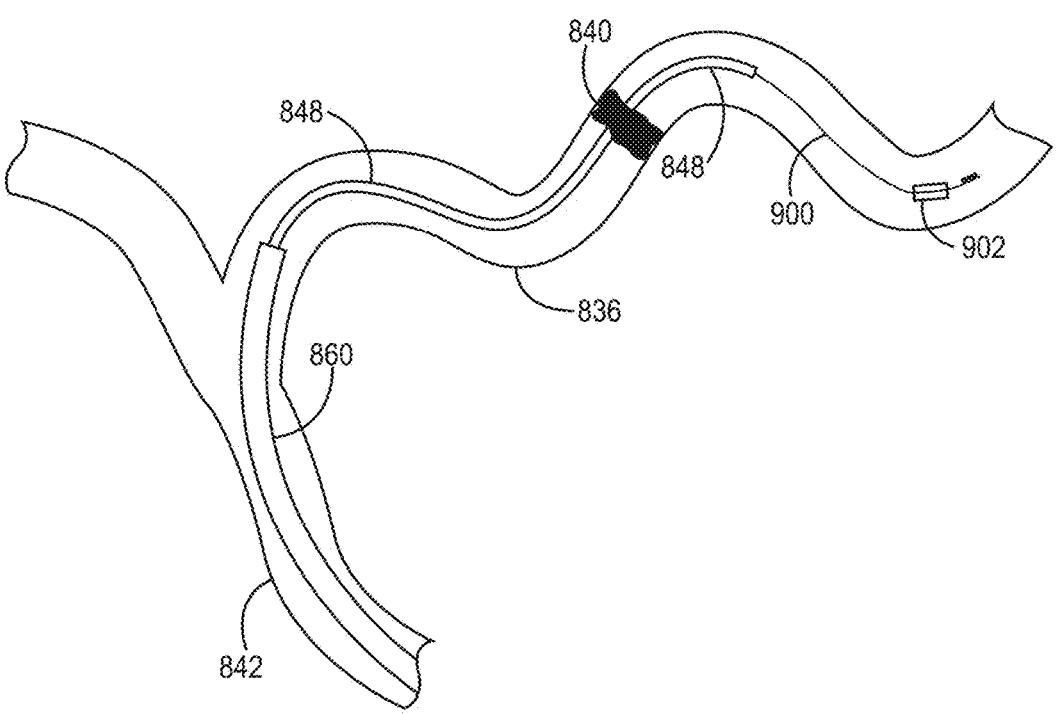
FIG. 39 is a fragmentary view of the cerebral artery depicted in FIG. 32 in which an alternative procedure comprises removal of the guidewire and replacement with a guide structure supporting a fiber based filter.

Referring to FIG. 40, cerebral artery 836 is shown with filter 902 deployed and a balloon/infusion catheter 904 in position. Balloon/infusion catheter 904 comprises balloon 906, infusion port(s) 908 and valve/seal 910, which inhibits flow into or out from the lumen of balloon/infusion catheter 904, see expanded view in insert of FIG. 40. The delivery of aspiration catheter 860 is described above in the context of FIG. 33, and these comments apply generally also in the context of FIGS. 39-42. In FIG. 39, aspiration catheter 860 is delivered earlier in the process relative to FIG. 33, which reflects choices available in the procedures.

Figure 41:
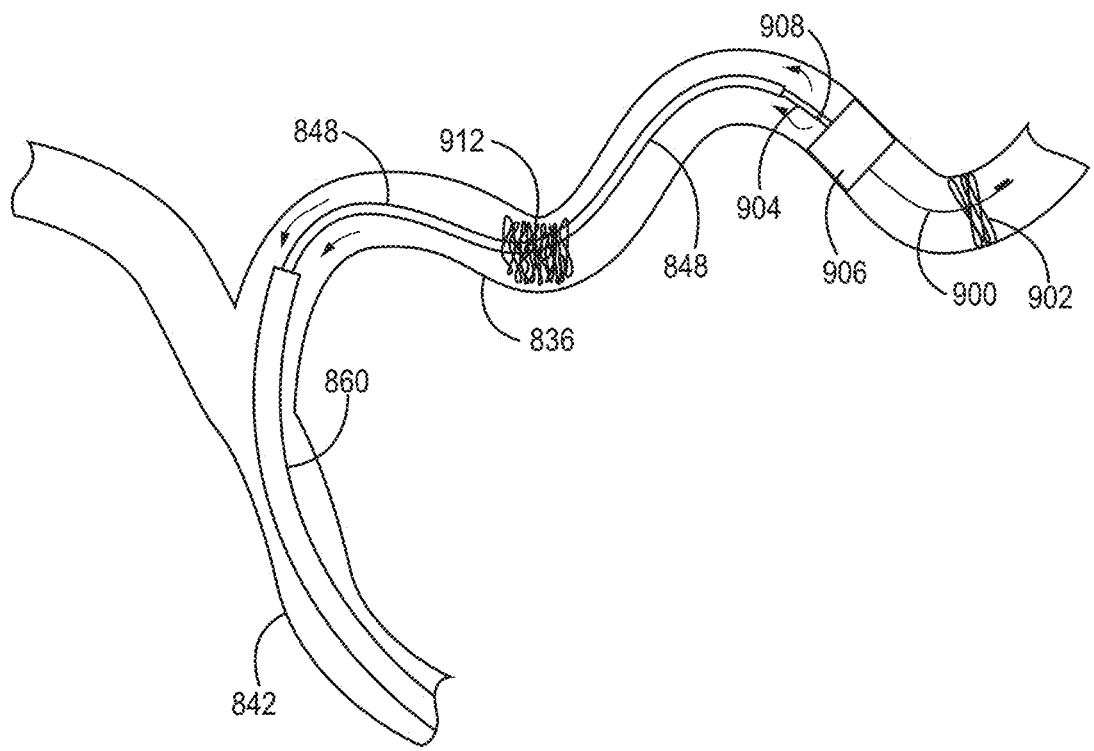
FIG. 41 is a fragmentary view depicting the cerebral artery of in FIG. 40 in which the balloon is inflated, the filter is deployed, and hydraulic forces are established with aspiration and infusion resulting in the proximal movement of thrombus from the clot.
Figure 42:
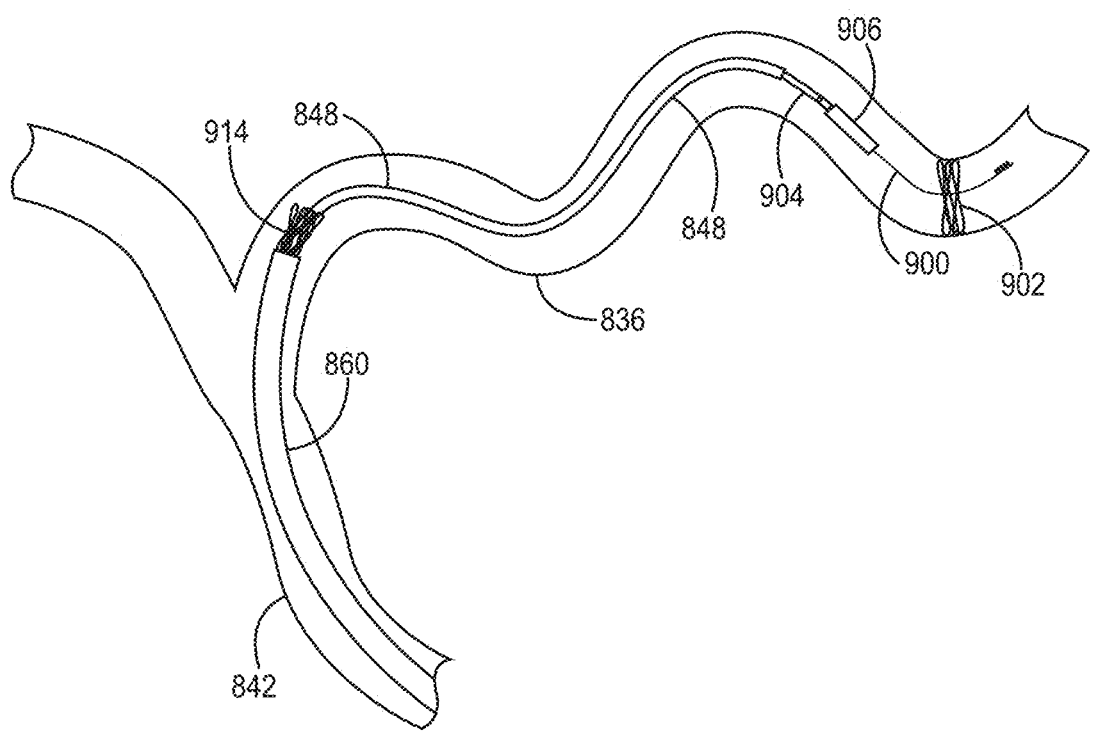
FIG. 42 is a fragmentary view depicting the cerebral artery of FIG. 41 in which thrombus has reached the distal opening into the aspiration catheter and the balloon is at least partially deflated in preparation for removal of the devices from the vessel.
Figure 43:
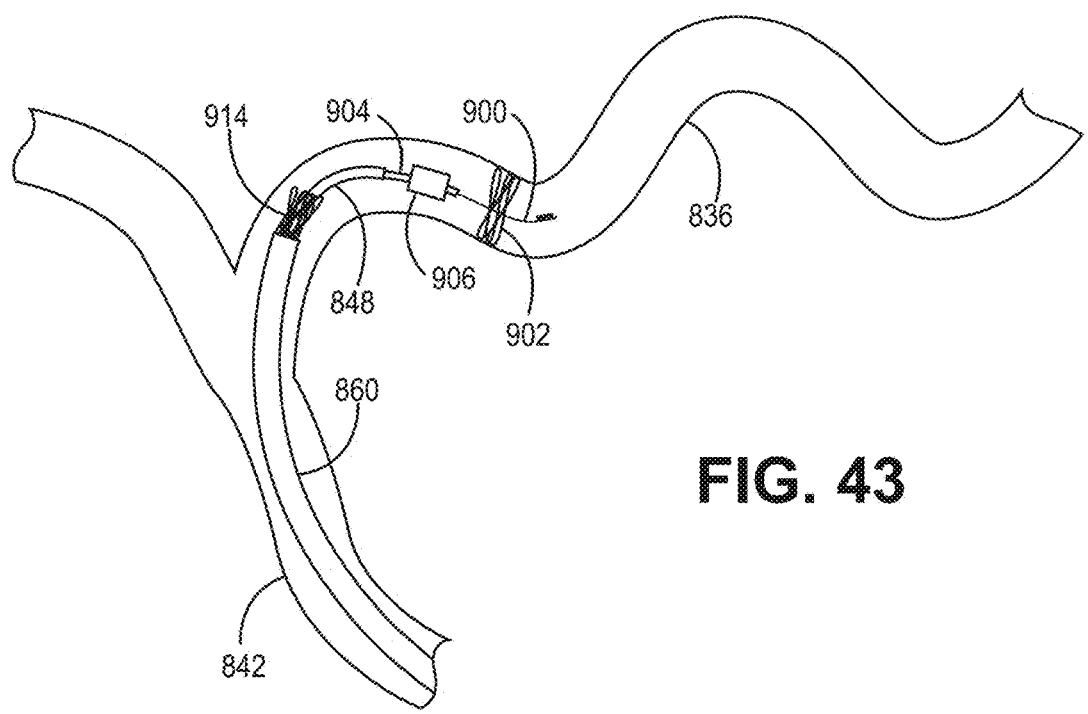
FIG. 43 is fragmentary view depicting the cerebral artery of FIG. 42 in which the microcatheter, balloon/infusion catheter, and deployed filter are moved toward the aspiration catheter for removal from the patient, in which the deployed filter is used to sweep the vessel on the way to removal.

Referring to FIG. 41, balloon 906 is inflated, aspiration is underway as indicated by flow arrows near the opening into aspiration catheter 860, and infusion is taking place as indicated by flow arrows near infusion port(s) 908. The resulting hydraulic forces induce proximal motion of thrombus 912 from clot 840. Fluid forces can be applied generally at least until thrombus is removed through aspiration catheter 860 or thrombus is secured as captured thrombus 914 at the opening of aspiration catheter 860, as shown in FIG. 42, or a combination of these effects. As shown in FIG. 42, balloon is then partially or approximately fully deflated for removal from the patient. With a polymer fiber-based filter 902, filter 902 can remain deployed during removal to capture emboli that may be formed at a risk to distal flow. Sweeping of filter 902 within cerebral artery 836, as shown in FIG. 43, can also collect loosened thrombus that was not carried with the flow. As shown in FIG. 43, microcatheter 848 and balloon/infusion catheter 904 are removed simultaneously with treatment device 900 and filter 902. As noted above, the order of removal of the devices generally is not significant within reason, but for these embodiments, it can be advantageous to bring filter 902 adjacent captured thrombus 914 and then remove filter 902 with aspiration catheter 860. Ultimately, all of the devices are removed from the patient, and the access location is sealed. Procedures using aspiration and a fiber based filter without infusion of liquid is also described in the '061 application.

Figure 44:
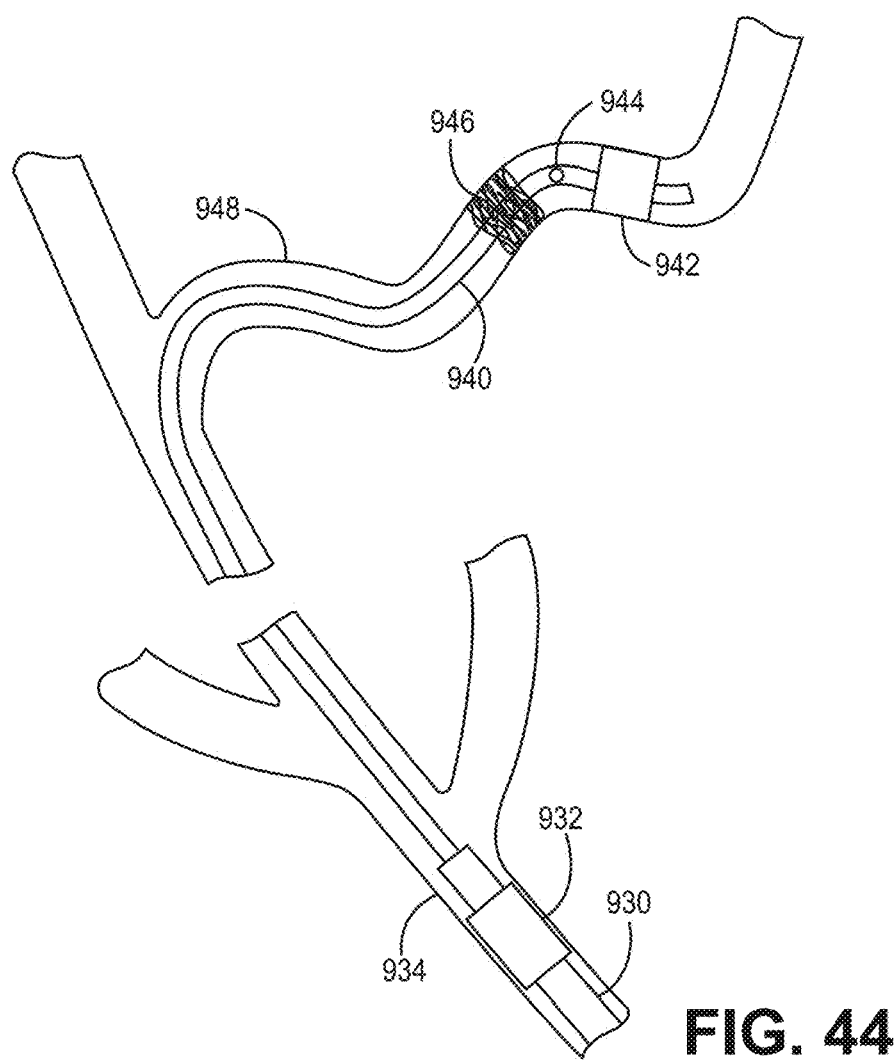
FIG. 44 is a fragmentary view of a carotid artery with a guide catheter placed in the carotid artery with a deployed balloon near the distal end of the guide catheter and with a balloon/infusion catheter extending form the guide catheter with a deployed balloon placed distal to a clot.

An embodiment of a therapeutic system with a guide catheter 930 comprising an occlusive balloon 932 is shown in FIG. 44. The distal end of guide catheter 930 is located in an internal carotid artery 934, although the distal end can be placed in a common carotid artery. As shown in FIG. 44, a balloon/infusion catheter 940 is positioned with an inflated balloon 942 and an infusion port(s) 944 positioned distal to clot 946 in a cerebral artery 948. When balloon 932 is expanded to occlude carotid artery 934, flow is blocked past the balloon so that pressure may be reduced against the clot as well as flow contrary to the aspiration in the vicinity of clot 946. Aspiration can be applied through the guide catheter in addition to or as an alternative to applying aspiration with a distinct aspiration catheter, as shown in FIGS. 31-43.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. To the extent that specific structures, compositions and/or processes are described herein with components, elements, ingredients or other partitions, it is to be understand that the disclosure herein covers the specific embodiments, embodiments comprising the specific components, elements, ingredients, other partitions or combinations thereof as well as embodiments consisting essentially of such specific components, ingredients or other partitions or combinations thereof that can include additional features that do not change the fundamental nature of the subject matter, as suggested in the discussion, unless otherwise specifically indicated.

What is claimed is:

1. A method for removing a clot from a patient's cerebral arteries, the method comprising:
   delivering a single lumen microcatheter over a guidewire positioned through the clot to place the distal end of the microcatheter at a distal position in a cerebral artery relative to the clot, wherein the microcatheter has an outer diameter at a distal portion from 1 Fr to 3 Fr;
   delivering a catheter with an occluding element through the microcatheter to place an un-deployed occluding element distal to the clot, wherein the occluding element comprises a balloon;
   occluding the cerebral artery with the occluding element distal to the clot wherein the cerebral artery is occluded prior to infusion of liquid;
   applying a hydraulic force by providing a first higher pressure to a distal end of the clot by infusing liquid between the clot and the occluding element from ports exclusively positioned distal to the clot to generate hydraulic forces on the distal end of the clot and providing a second lower pressure to a proximal end of the clot by aspirating liquid from the cerebral artery proximal to the clot with at least some temporal overlap of infusing and aspirating to push the clot in a distal to proximal direction relative to the microcatheter, wherein the lower pressure is applied with an aspiration catheter having a distal aspiration opening within cerebral arteries, and wherein the hydraulic force is directed towards the clot without prior mechanical fragmentation.

2. The method of claim 1 wherein aspiration for aspirating liquid is provided by the aspiration catheter and the aspiration catheter is delivered over the microcatheter.

3. The method of claim 1 wherein the occluding element comprises a balloon and wherein the microcatheter is positioned with its distal opening distal to the clot and from about 0.25 cc to about 25 cc of infusion liquid is delivered from the microcatheter.

4. The method of claim 1 wherein the catheter with the occluding element comprises a balloon catheter with a balloon, the balloon catheter comprising the ports proximal to the balloon, and wherein the balloon catheter is positioned with the balloon and the ports distal to the clot and the balloon occludes the vessel while from about 0.25 cc to about 25 cc of liquid is infused from the ports.

5. The method of claim 4 wherein a single lumen balloon/infusion catheter is used to provide the balloon and the ports.

6. The method of claim 5 wherein a size and number of the ports are selected to provide appropriate infusion at pressures inflating the balloon.

7. The method of claim 4 wherein a two lumen balloon/infusion catheter is used to provide the balloon and the ports.

8. The method of claim 4 wherein the catheter comprises a catheter shaft with a distal end, the distal end of the catheter shaft comprising a distal wire or coil extending in a distal direction, or a distal end of the balloon catheter comprises a guidewire port and a valve/seal is located at or near to the guidewire port with a configuration to engage a guidewire to reduce or eliminate liquid flow to or from the guidewire port.

9. The method of claim 1 wherein a proximal most edge of the ports are no more than about 5 centimeters from a proximal most edge of the occluding element.

10. The method of claim 1 wherein liquid from the cerebral artery proximal to the clot is aspirated through a suction extension, the suction extension comprising a suction tip extendable beyond a guide catheter; and a proximal portion forming a tight fit with an interior wall of the guide catheter.

11. The method of claim 1 wherein a polymer valve covers the ports, the polymer valve configured to open at a sufficient pressure thereby controlling flow from the ports.

12. The method of claim 1 wherein the catheter with the occluding element comprises proximal fittings comprising a Y-branch fitting providing a first connector for attachment of an infusion fluid source for delivery through the ports and a second connector for attachment of a device configured for delivery and/or removal of balloon expansion fluid.

13. The method of claim 1 wherein the aspiration catheter is positioned over an infusion catheter.

14. The method of claim 1 wherein aspiration is initiated after the vessel is occluded.

15. The method of claim 1 wherein aspiration and infusion are initiated approximately simultaneously.

16. The method of claim 1 wherein aspiration and infusion are initiated sequentially.

17. The method of claim 1 wherein aspiration is maintained after removal of the clot while removing the occluding element from the vessel.

18. A method for removing a clot from a patient's cerebral artery, the method comprising:
   delivering a catheter with an occluding element through a microcatheter with a distal opening distal to the clot to place an un-deployed occluding element distal to the clot in the cerebral artery;
   occluding the cerebral artery with the occluding element distal to the clot;
   creating a differential pressure across the clot by infusing liquid between the clot and the occluding element from ports exclusively positioned distal to the clot to generate hydraulic forces on a distal end of the clot and aspirating liquid from the cerebral artery proximal to the clot with at least some temporal overlap of infusing and aspirating to push the clot in a distal to proximal direction, wherein a distal end of an aspiration catheter is within the cerebral arteries, and wherein the hydraulic force is directed towards the clot without prior mechanical fragmentation,
   wherein aspiration for aspirating liquid is provided by the aspiration catheter delivered over the catheter with the occluding element, wherein the occluding element comprises a balloon and wherein the microcatheter is located over the catheter with the occluding element with its distal opening distal to the clot and from about 0.25 cc to about 25 cc of infusion liquid is delivered from the microcatheter.

* * * * *